United States Patent
Xue et al.

(10) Patent No.: US 11,680,267 B2
(45) Date of Patent: *Jun. 20, 2023

(54) CO-REGULATORY SEQUENCES BASED ON TETRACYCLINE AND CUMATE

(71) Applicant: Shenzhen Eureka Biotechnology Co., Ltd., Guandong (CN)

(72) Inventors: Bofu Xue, Guangdong (CN); Yinhui Yang, Guangdong (CN); Ke Liu, Guangdong (CN); Mo Ma, Guangdong (CN)

(73) Assignee: Shenzhen Eureka Biotechnology Co., Ltd., Guangdong (CN)

(*) Notice: Subject to any disclaimer, the term of this patent is extended or adjusted under 35 U.S.C. 154(b) by 0 days.

This patent is subject to a terminal disclaimer.

(21) Appl. No.: 17/766,685

(22) PCT Filed: Sep. 16, 2020

(86) PCT No.: PCT/CN2020/115520
§ 371 (c)(1),
(2) Date: Apr. 5, 2022

(87) PCT Pub. No.: WO2021/232632
PCT Pub. Date: Nov. 25, 2021

(65) Prior Publication Data
US 2022/0364103 A1 Nov. 17, 2022

(30) Foreign Application Priority Data
May 22, 2020 (CN) .......................... 202010442506.3

(51) Int. Cl.
*C12N 15/63* (2006.01)
*C12N 15/85* (2006.01)

(52) U.S. Cl.
CPC .......... *C12N 15/635* (2013.01); *C12N 15/85* (2013.01); *C12N 2800/10* (2013.01); *C12N 2800/22* (2013.01); *C12N 2830/001* (2013.01); *C12N 2830/003* (2013.01)

(58) Field of Classification Search
CPC ............ C12N 15/635; C12N 2830/001; G01N 2500/02
See application file for complete search history.

(56) References Cited

U.S. PATENT DOCUMENTS

| | | |
|---|---|---|
| 5,464,758 A | 11/1995 | Gossen |
| 5,654,168 A | 8/1997 | Bujard et al. |
| 5,789,156 A | 8/1998 | Bujard et al. |
| 5,814,618 A | 9/1998 | Bujard et al. |
| 5,888,981 A | 3/1999 | Bujard et al. |
| 6,004,941 A | 12/1999 | Bujard et al. |
| 6,087,166 A | 7/2000 | Baron et al. |
| 6,136,954 A | 10/2000 | Bujard et al. |
| 6,271,341 B1 | 8/2001 | Baron et al. |
| 6,271,348 B1 | 8/2001 | Bujard et al. |
| 6,914,124 B2 | 7/2005 | Bujard et al. |
| 7,541,446 B2 | 6/2009 | Hillen et al. |
| 7,745,592 B2 | 6/2010 | Massie et al. |
| 8,383,364 B2 | 2/2013 | Berkhout et al. |
| 9,181,556 B2 | 11/2015 | Bujard et al. |

FOREIGN PATENT DOCUMENTS

| | | |
|---|---|---|
| WO | WO1996001313 A1 | 1/1996 |
| WO | WO2000075347 A2 | 12/2000 |
| WO | WO2002020811 A2 | 3/2002 |
| WO | WO2002088346 A2 | 11/2002 |
| WO | WO2006037215 A1 | 4/2006 |

OTHER PUBLICATIONS

Broussau et al. Inducible packaging cells for large-scale production of lentiviral vectors in serum-free suspension culture. Molecular Therapy, vol. 16, No. 3, pp. 500-507, and 1/2-2/2 of Supplemental Figures, Mar. 2008. (Year: 2008).*
Ternette et al. Expression of RNA virus proteins by RNA polymerase II dependent expression plasmids is hindered at multiple steps. Virology Journal, vol. 4, 51, Jun. 5, 2007, printed as pp. 1/10-10-10. (Year: 2007).*
Clontech. pTet-On Advanced Vector Information, from www.clonech.com, pp. 1-2, Aug. 16, 2010 (Year: 2010).*
Akef et al., "Splicing promotes the nuclear export of beta-globin mRNA by overcoming nuclear retention elements," RNA Sep. 2015, 21(11):1908-1920.
Gossen et al., "Tight control of gene expression in mammalian cells by tetracycline-responsive promoters," Proceedings of the National Academy of Sciences, Jun. 1992, 89(12):5547-5551.
International Search Report and Written Opinion in International Appln. No. PCT/CN2020/115520, dated Feb. 25, 2021, 13 pages (with English translation).
Kallunki et al., "How to choose the right inducible gene expression system for mammalian studies," Cells, Jul. 2019, 8(796).

(Continued)

*Primary Examiner* — Jennifer Dunston
(74) *Attorney, Agent, or Firm* — Fish & Richardson P.C.

(57) ABSTRACT

The present disclosure provides a nucleic acid sequence for regulating the transcription of a nucleic acid fragment of interest, wherein the nucleic acid sequence comprises at least 2 copies of TetO-operator sequences capable of binding to a transactivator rtTA regulatable by tetracycline or a derivative thereof, and 1 copy of minimal promoter sequence containing a TATA box sequence, and at least 1 copy of a CuO-operator sequence capable of binding to a transcription repressor CymR regulatable by cumate. The present disclosure also provides a vector and a host cell containing the nucleic acid sequence, and a method for inducing the expression of a nucleic acid fragment of interest in a host cell.

20 Claims, 4 Drawing Sheets
Specification includes a Sequence Listing.

(56) References Cited

OTHER PUBLICATIONS

Kraeva et al., "Tetracycline-inducible gene expression system in Leishmania mexicana," Molecular & Biochemical Parasitology, Nov. 2014, 198(1):3 pages.

Li et al., "An efficient cumate-inducible system for procyclic and bloodstream form Trypanosoma brucei," Molecular & Biochemical Parasitology, Jun. 2017, 214: 16 pages.

Loew et al., "Improved Tet-responsive promoters with minimized background expression," BMC Biotechnology, Nov. 2010, 10:81.

Mullick et al., "The cumate gene-switch: a system for regulated expression in mammalian cells," BMC biotechnology, Dec. 2006, 6:18 pages.

Sato et al., "Generation of mouse iPS cells using an inducible expression of transgenes via the cumate gene-switch," Analytical Biochemistiy, Apr. 2020, 599: 7 pages.

Zhou et al., "Optimization of the Tet-On system for regulated gene expression through viral evolution," Gene therapy, Oct. 2006, 13(19):1382-1390.

* cited by examiner

CO-REGULATORY SEQUENCES BASED ON TETRACYCLINE AND CUMATE

CROSS-REFERENCE TO RELATED APPLICATIONS

This application is a National Stage application under 35 U.S.C. § 371 of International Application No. PCT/CN2020/115520, filed Sep. 16, 2020, which claims priority to Chinese Application No. 202010442506.3, filed May 22, 2020, both of which are considered part of the disclosure of this application, and are incorporated in their entirety into this application.

SEQUENCE LISTING

This application contains a Sequence Listing that has been submitted electronically as an ASCII text file named 52392-0004US1_SEQ.txt. The ASCII text file, created on Apr. 8, 2022, is 36 kilobytes in size. The material in the ASCII text file is hereby incorporated by reference in its entirety.

TECHNICAL FIELD

The present disclosure relates to a tetracycline-based and Cumate-dependent nucleic acid sequence for regulating the transcription of a nucleic acid fragment of interest. Specifically, the present disclosure relates to a nucleic acid sequence for regulating the transcription of a nucleic acid fragment of interest, wherein the nucleic acid sequence comprises at least two copies of TetO-operator sequences (Tet operator, TetO) binding to a reverse tetracycline controlled transactivator (rtTA), one copy of a minimal promoter sequence containing the TATA box sequence, and at least one copy of a CuO-operator sequence (Cumate operator, CuO) binding to the CymR transcription repressor. Furthermore, there is a spliceable intron sequence between the 3' end downstream of the aforementioned nucleic acid sequence and the 5' end upstream of the regulated nucleic acid fragment of interest, which can be used to further improve the transcription activity after induction without induction leakage. Still further, the present disclosure also relates to a vector, viruses, cell, transgenic plant or animal containing the above regulatory sequence.

BACKGROUND

The regulation of gene expression can be achieved by regulating several steps in gene expression, including transcription, RNA splicing, translation, and post-translational modification, wherein the regulation of specific gene(s) or nucleic acid fragment(s) of interest in the transcription step is the most extensive and effective way for gene expression regulation. An inducible expression system that controls the transcription and expression of specific gene(s) and nucleic acid fragment(s) in cells, plants or animals is turned on or off through exogenous factor(s), and it plays a key role in the fields of basic biological research, biopharmaceuticals, gene therapy, cell therapy, improvement of transgenic plants or animals. Generally, the design of an inducible expression system is composed of two parts: 1) a specific nucleic acid sequence upstream of the 5' end of the regulated nucleic acid fragment of interest, which can generally be combined with a transcription activator or repressor to regulate the transcription of the nucleic acid fragment of interest; an example of such a specific nucleic acid sequence (hereinafter, a response element) is a nucleic acid sequence containing an operator; 2) a single or multiple regulator(s), which can bind to or be separated from the above specific nucleic acid sequence under the control of an external factor(s) and generally has a function of transcriptional activation or repression, and which is usually an expressed protein. The external factor(s) can be an environmental factor, such as temperature, light, etc.; or a certain component, such as metabolites, hormones, metal ions, or artificial compounds involved in life activities.

"Tetracycline inducible system (or Tet System)" is currently one of the most widely used inducible expression systems in scientific research and business (see, for example, Gossen, M. and H. Bujard (1992). "Tight control of gene expression in mammalian cells by tetracycline-responsive promoters." Proc Natl Acad Sci USA 89(12): 5547-5551., U.S. Pat. Nos. 5,888,981, 5,814,618, 6,004,941, 5,814,618, 7,541,446, WO96/01313 and WO00/75347 (incorporated herein by reference)). It is mainly composed of a tetracycline-dependent regulator and a response element containing a TetO operator, and regulates the transcription of a nucleic acid fragment of interest linked to the response element containing a TetO operator in a tetracycline-inducible way. The response element containing a TetO operator can bind to a transcription activator in the absence of tetracycline, and after binding, initiate the transcription of the downstream regulated nucleic acid fragment of interest; it can also be placed downstream of a constitutively active promoter and upstream of the regulated nucleic acid fragment of interest, and can bind to a tetracycline-dependent repressor in the absence of tetracycline to inhibit the transcription of the regulated nucleic acid fragment of interest at downstream. Traditionally, the tetracycline-dependent regulator binds to the TetO operator in the absence of tetracycline, and can be separated from the TetO operator in the presence of tetracycline. For example, an activator designed based on this principle can initiate the transcription of the regulated nucleic acid fragment of interest by removing tetracycline in the environment (U.S. Pat. Nos. 5,464,758, 6,914,124, 5,789,156, 6,271,348, WO96/01313 and WO00/75347). Later, a trans-tetracycline-dependent regulator was developed, which only binds to the TetO operator in the presence of tetracycline. The trans-tetracycline-dependent activator can activate the transcription of the regulated nucleic acid fragment of interest by adding tetracycline to the environment (U.S. Pat. Nos. 5,654,168, 6,136,954, 5,789,156, 6,271,348, 6,087,166, 6,271,341, 7,541,446, WO96/01313 and WO00/75347); for example, the transcription of the regulated nucleic acid fragment of interest can be activated by adding tetracycline to the medium, or the transcription and expression of the regulated gene of interest introduced by genetic engineering can be activated by injecting tetracycline into the transgenic animal.

The transcription activity of the regulated nucleic acid fragment under induction conditions and the leaky transcription activity of the regulated nucleic acid fragment under non-induction conditions are two important indicators for evaluating an inducible expression system. A good inducible expression system needs to have a higher induced transcription activity and a lower leaky transcription activity. The tetracycline inducible system has been optimized by many laboratories since the first report, and its performance has been continuously improved. The main optimizations include the optimization of the tetracycline-dependent regulator and the response element containing a TetO operator. The optimization of the tetracycline-dependent regulator mainly focuses on (1) reducing the leaky transcription activity under non-induction conditions while maintaining the induced transcription activity as much as possible, and increasing the ratio of induced/leaky transcription activity; (2) optimizing the specificity and affinity of the regulator and tetracycline and a derivative thereof as inducers, to achieve a maximum transcription activity at a lower concentration of tetracycline and a derivative thereof, and at the same time to reduce the affinity of the regulator to the response element in the absence of the inducer. (See Zhou, X., et al. (2006). "Optimization of the Tet-On system for regulated gene expression through viral evolution." Gene Ther 13(19): 1382-1390., U.S. Pat. Nos. 8,383,364, 7,541,446). The optimization of the response element containing a TetO operator mainly focuses on (1) optimizing the copy number and linkage sequence of the TetO operator; enhancing the stability of multiple copies of a continuous TetO operator sequence, especially in viral vectors, while improving the performance of the response element; (2) under the condition that does not significantly affect the transcription activity after induction, reducing the non-induction leaky transcription activity of the minimal promoter and increasing the ratio of induced/leaky transcription activity (see Loew, R., et al. (2010). "Improved Tet-responsive promoters with minimized background expression." BMC Biotechnol 10: 81., U.S. Pat. No. 9,181,556). The commercial tetracycline inducible systems currently widely used are mainly those from Clontech Laboratories, Inc., such as Tet-On® Advanced Inducible Gene Expression Systems (document number: PT3898-1 (102312), wherein the tetracycline-dependent transactivator rtTA and the TetO Operator-containing response element TRE (a nucleic acid sequence containing multiple copies of continuous TetO operator sequences and a minimal promoter sequence, Tet Response Element, hereinafter referred to as TRE) are hereinafter referred to as rtTA$_{adv}$ and TRE$_{adv}$), Tet-Off® Advanced Inducible Gene Expression Systems (document number: PT3945-1 (101612)) and Tet-On® 3G Inducible Expression Systems (document number: PT5148-1 (010814), wherein the tetracycline-dependent regulator rtTA and the TetO operator-containing response element TRE are hereinafter referred to as rtTA$_{3G}$ and TRE$_{3G}$ respectively).

Cumate Inducible System is developed from the p-cym operon of *Pseudomonas putida*, and is composed of a CuO operator downstream of the TATA box of the constitutively active promoter and a repressor CymR protein which is Cumate/a derivative thereof-dependent and can bind to the CuO operator. In the absence of Cumate, the CymR protein binds to the CuO operator to inhibit the transcription of the downstream regulated nucleic acid fragment of interest; when the CymR protein binds to Cumate, the affinity of CymR protein with the CuO operator decreases and thus they are separated from each other, and the transcription of the downstream regulated nucleic acid fragment of interest is no longer inhibited. For example, the CuO operator is placed between the regulated nucleic acid fragment of interest and the constitutively active promoter sequence, and the CymR repressor is constitutively and actively expressed in the cell. When there is no inducer (Cumate or a derivative thereof) in the medium, the binding of the expressed CymR protein to the CuO operator inhibits the transcription of the regulated nucleic acid fragment of interest; when the inducer is added to the medium, the CymR protein that binds to Cumate or its derivative is separated from the CuO operator, and the transcription of the regulated nucleic acid fragment of interest is no longer inhibited (see WO02088346A2, WO2006037215A1 (incorporated herein by reference)).

The optimization of Cumate inducible system mainly focuses on: (1) optimizing the shortest effective CuO operator sequence; (2) screening for inducers of Cumate and a derivative thereof that are soluble in water and have similar functions to p-cumate; (3) constructing an inducible system similar to Tet-Off, which consists of a CymR activator (such as constructing a fusion protein of CymR and HSV VP-16 transcription activation-domain) and a response element containing multiple copies of continuous CuO operators (the sequence contains multiple repeats of the CuO sequence and a downstream minimal promoter). In the absence of Cumate inducer, the binding of the CymR activator with the CuO operator activates the transcription of the regulated nucleic acid fragment of interest; in the presence of Cumate inducer, the CymR activator and the CuO operator are separated from each other, and the transcription of the regulated nucleic acid fragment of interest stops. (4) constructing an inducible system similar to Tet-On, which consists of a trans-CymR activator and a response element containing multiple copies of continuous CuO operators (which is obtained by mutation and screening, and allowing the trans-CymR to bind to the CuO operator in the presence of a Cumate inducer and to be separated from the CuO operator in the absence of a Cumate inducer, and constructing a fusion protein of trans-CymR and HSV VP-16 transcription activation-domain as the trans-CymR activator). In the presence of a Cumate inducer, the trans CymR activator binds to the response element to activate the transcription of the regulated nucleic acid fragment of interest; in the absence of Cumate inducer, the trans CymR activator is separated from the response element, and the transcription of the regulated nucleic acid fragment of interest stops (see Mullick, A., et al. (2006). "The cumate gene-switch: a system for regulated expression in mammalian cells." BMC Biotechnol 6: 43.; WO02088346A2, WO2006037215A1). The currently widely used Cumate inducible system is mainly the SparQ Cumate Switch system from SBI System Biosciences (document number: 1-090810).

In the current development and improvement of various inducible expression systems, the main optimizations are focused on reducing the basic leaky transcription activity of the regulated nucleic acid fragment of interest under non-induction conditions, and the transcription activity under induction conditions is not the focus of optimization. As a result, the transcription activity of the nucleic acid fragment of interest regulated by the inducible expression system is lower than the transcription activity under the control of a common constitutively active promoter. In the development of biotechnology, it is equally important to improve the absolute transcription activity of the nucleic acid fragment of interest after induction and to control its leaky transcription activity under non-induction conditions. For example, in the field of biopharmaceuticals, the production of a cytotoxic recombinant protein or virus vector requires not only to increase the expression level of the protein encoded by the nucleic acid fragment of interest after induction, but also to control the leaked expression level of the nucleic acid fragment of interest under non induction conditions in order to ensure the culture state and stability of the producer cell line. Therefore, an inducible expression system that can not only increase the transcription activity of the nucleic acid fragment of interest under induction conditions, but also control the leaky transcription activity of the nucleic acid fragment of interest under non-induction conditions can widely promote the research, development and industrialization of biotechnology in many fields.

SUMMARY

The present disclosure relates to a tetracycline and Cumate-dependent nucleic acid sequence capable of regulating the transcription of a nucleic acid fragment of interest. Specifically, the nucleic acid sequence comprises at least two copies of TetO-operator sequences (Tet operator, TetO) binding to a reverse tetracycline/derivatives thereof controlled transactivator (rtTA), one copy of a minimal promoter sequence containing a TATA box sequence, and at least one copy of CuO-operator sequence (Cumate operator, CuO) binding to a CymR transcription repressor. Furthermore, a spliceable intron sequence between the 3' end downstream of the aforementioned nucleic acid sequence and the 5' end upstream of the regulated nucleic acid fragment of interest can be used to further improve the transcription activity after induction without induction leakage. Still further, the present disclosure also relates to a vector, viruses, cell, transgenic plant or animal containing the above regulatory sequences for regulating gene expression.

The term "nucleic acid fragment of interest" may generally refer to a deoxyribonucleic acid fragment (DNA fragment), and according to the application purpose, may refer to a gene, such as a nucleic acid sequence encoding a protein; it can be a fragment of ribonucleic acid (RNA), such as a RNA fragment of the whole or part genome of an RNA virus, microRNA (miRNA), small interfering RNA (siRNA), long non-coding RNAs (LncRNA), guide RNA for CRISPR gene editing system (gRNA), transfer RNA (tRNA), ribosomal RNA (rRNA), an aptamer, a ribonucleic acid fragment that can bind to another nucleic acid, a ribonucleic acid fragment that can bind to a specific protein, or any ribonucleic acid fragment; it can also be a combination of the above one or more nucleic acid sequence(s).

The term "vector" is a nucleic acid-containing molecule that is usually used as a vehicle for artificially transporting a foreign genetic material, such as the above-mentioned nucleic acid fragment of interest, into another cell, where it is replicated and/or expressed. Functionally, all vectors can be used to clone and carry a foreign nucleic acid fragment of interest, and there are expression vectors specifically designed for transcription of a nucleic acid fragment and expression of a protein. Plasmids, viral vectors, cosmids and artificial chromosomes are the four main types of vectors. Among these, the most commonly used vector is plasmids. All engineered plasmid vectors contain an origin of replication for replication in bacteria, a multiple cloning site for insertion of a nucleic acid fragment of interest, and a marker gene for selection of positive strains. The viral vector is another commonly used vector, and is commonly used to deliver a genetic material, such as a nucleic acid fragment of interest, into cells. This process can be carried out in vivo or in cell culture (in vitro). The nucleic acid fragment of interest can be efficiently introduced into the infected target cell based on various molecular mechanisms evolved by the virus itself, such as protection of the genetic material, selection of host cells based on the recipient, delivery of genetic material into the host cell, replication and/or expression in the host cell, modulation of host cell growth, metabolism, reproduction, replication and defense mechanisms, as well as suppression and/or escape of the immune system in higher animals. In addition to being used in molecular biology research, viral vectors are also commonly used in gene therapy, cell therapy, immunotherapy, and vaccine development.

Generally, an inducible expression system will also increase the leaky transcription activity under non-induction conditions when enhancing the induced transcription activity of the nucleic acid fragment of interest; and the commonly used strategies to control the leaky transcription activity under non-induction conditions, such as reducing the affinity of the transactivator with the operator in the absence of an inducer by point mutation or reducing the basic activity of the minimal promoter downstream of the operator, will affect the maximum transcription activity after induction. This makes most of the single inducible expression systems with the purpose of balancing the leaky transcription activity under non-induction conditions have reduced transcription activation activity for the nucleic acid fragment of interest under induction conditions. Designing a complex inducible expression system containing multiple regulatory components is an effective direction to solve the above problem. In the complex inducible expression system realized by the present disclosure, on the one hand, the maximum transcription activity after induction of the combination of the activator and the corresponding response element in a first inducible expression system is optimized, and on the other hand, the leaky transcription activity of the complex inducible expression system is controlled by using the combination of a repressor and the corresponding response element in a second inducible expression system; for example, the Tet-On inducible expression system is used as the first inducible expression system, and the Cumate inducible expression system is used as the second inducible expression system. The complex response element sequence of the above-mentioned complex inducible expression system contains at least two copies of TetO operator sequences (Tet operator) binding to a reverse tetracycline/derivative thereof controlled transactivator (rtTA), one copy of a minimal promoter sequence containing a TATA box sequence, and at least one copy of a CuO operator sequence (CuO operator) binding to a CymR transcription repressor.

The inventors have found that the induced transcription activity and the non-induced leaky transcription activity of the Tet-On and Cumate complex inducible expression system are affected by the following factors: (1) multiple copies of TetO operators and its linkage nucleic acid sequence; (2) the minimal promoter sequence in the TRE response element; (3) the relative position of the CuO operator and the TATA box in the minimal promoter. The control of the $TRE_{3G}$ response element in the third-generation Tet-On system is more stringent than that of the $TRE_{adv}$ response element in the second-generation Tet-On system, and has a lower non-induced leaky transcription activity; the closer the distance between the CuO operator and the TATA box, the stricter the control of leaky transcription activity, but the effect on the induced transcription activity becomes greater; the farther the distance between the CuO operator and the TATA box, the weaker the control of leaky transcription activity, but the effect on the induced transcription activity becomes smaller. Based on the above findings, the nucleic acid sequence of the present disclosure for regulating the transcription of the nucleic acid fragment of interest contains: at least 2 copies (for example, 2, 3, 4, 5, 6, 7 or more, preferably 7) of a TetO-operator sequence binding to the reverse tetracycline/a derivative thereof-controlled transactivator rtTA, preferably, the TetO-operator sequence is shown in SEQ ID NO: 24; a minimal promoter sequence containing a TATA box sequence, preferably the minimal promoter sequence is shown in SEQ ID NO: 25 or SEQ ID NO: 26, more preferably the minimal promoter sequence is shown in SEQ ID NO: 25; and a CuO-operator sequence binding to a transcription repressor CymR regulated by cumate, preferably the CuO operator sequence is shown in SEQ ID NO:27. Preferably, at least one CuO operator sequence is located downstream of the above-mentioned promoter TATA box, preferably 10 bp to 100 bp downstream of the TATA box, such as 14 bp, 30 bp, 50 bp and 100 bp; further preferably, there is only one CuO sequence located at 30 bp to 50 bp downstream of the TATA box; still further, there is only one CuO sequence located at 30 bp or 50 bp downstream of the TATA box. Preferably, the nucleic acid sequence of the present disclosure for regulating the transcription of the nucleic acid fragment of interest is set forth in SEQ ID NO: 23, SEQ ID NO: 28, SEQ ID NO: 29 or SEQ ID NO: 30, more preferably, set forth in SEQ ID NO:23 or SEQ ID NO:28.

Introns downstream of the promoter in the expression plasmid can generally increase the stability of messenger RNA (mRNA) and increase the efficiency of mRNA transport out of the nucleus (see Akef, A., et al. (2015). "Splicing promotes the nuclear export of beta-globin mRNA by overcoming nuclear retention elements." RNA 21(11): 1908-1920) and increase the expression of a nucleic acid fragment of interest. The inventors have found that linking a spliceable intron downstream of the 3' end of the response element in a single inducible expression system can also increase the expression of the regulated nucleic acid fragment of interest after induction, but at the same time it will significantly increase the non-induced leaky expression of the nucleic acid fragment of interest. Linking a spliceable intron sequence between the downstream of the 3' end of the tetracycline and Cumate-dependent complex response element sequence and the upstream of the 5' end of the regulated nucleic acid fragment of interest can significantly increase the induced expression level without significantly increasing the non-induced leaky expression level. Based on this, in the present disclosure, preferably, a spliceable intron fragment is linked between the downstream of the 3' end of the tetracycline and Cumate-dependent complex response element sequence and the upstream of the 5' end of the nucleic acid fragment of interest. There is no specific limitation on the selection of the above-mentioned intron, and those skilled in the art will understand that any sequence capable of performing RNA splicing in mammalian cells can achieve the above functions. Intron sequences that may be selected include, but are not limited to, introns on commonly used cloning vectors, such as a rabbit β-globulin intron, a hybrid intron derived from human β-globulin and immunoglobulin heavy chain intron, EF-1α intron A, SV40 intron, a hybrid intron derived from adenovirus and immunoglobulin heavy chain intron, a modified human cytomegalovirus intron, a hybrid intron derived from chicken β-actin (CBA) and mouse microvirus (MMV) intron, a chimera derived from chicken β-actin and rabbit β-globulin intron, and a mP1 intron; or any intron of any gene of any eukaryote; or an artificial intron sequence designed based on the intron splicing rules. The intron sequence used in the examples of the present disclosure may be set forth in SEQ ID NO: 31.

In the above-mentioned Tet-On and Cumate complex inducible expression system, in the absence of tetracycline or a derivative thereof and a Cumate inducer (Cumate or a functional analogue), the rtTA transactivator cannot bind to the complex response element, and the binding of the CymR repressor and the CuO operator in the complex response element further inhibits the leaky transcription activity of the regulated nucleic acid fragment of interest caused by the non-specific binding of rtTA transactivator or the basic activity of minimal promoter; in the presence of Cumate inducer alone, neither the rtTA transactivator nor the CymR repressor binding to the Cumate inducer can bind to the complex response element, the non-specific binding of rtTA transactivator or the basic activity of minimal promoter results in little transcription of the regulated nucleic acid fragment of interest; in the presence of tetracycline or a derivative thereof alone, the binding of the rtTA transactivator and the TetO operator in the complex response element activates the transcription of the regulated nucleic acid fragment of interest, but the CymR repressor also binds to the CuO operator in the complex response element, which leads to a limited transcription of the regulated nucleic acid fragment of interest; in the presence of both tetracycline or a derivative thereof and a Cumate inducer, the rtTA transactivator binds to the TetO operator in the complex response element, and the CymR repressor binding to the Cumate inducer is separated from the CuO operator in complex response element, thereby the most active transcription of the regulated nucleic acid fragment of interest is obtained. The nucleic acid coding sequence of the rtTA transactivator is preferably human codon-optimized SEQ ID NO: 18; CymR is preferably human codon-optimized SEQ ID NO: 15.

The above-mentioned Tet-On and Cumate complex inducible expression system can be applied in basic biological scientific research, biopharmaceuticals, gene therapy, cell therapy, improvement of transgenic plants or animals, including but not limited to controlling the turn-on or -off of transcription of protein-coding nucleic acid sequences in cells, animals or plants; controlling the turn-on and -off of transcription of non-protein-coding nucleic acid sequences, such as a RNA fragment of the whole or part genome of an RNA virus, microRNA (miRNA), small interfering RNA (siRNA), long non-coding RNAs (LncRNA), guide RNA for CRISPR gene editing system (gRNA), transfer RNA (tRNA), ribosomal RNA (rRNA), an aptamer, a ribonucleic acid fragment that can bind to another nucleic acid, a ribonucleic acid fragment that can bind to a specific protein, or any ribonucleic acid fragment; it can also be a combination of the above one or more nucleic acid sequence(s). In one aspect, the above-mentioned Tet-On and Cumate complex inducible expression system can be used to express and produce a virus vector in the field of gene therapy, cell therapy or immunotherapy; to express and produce a cytotoxic or unstable protein; to express and produce an attenuated vaccine or viral like particle (VLP) vaccine in the field of vaccines; to control the turn-on or turn-off of transcription and expression of a nucleic acid fragment of interest in transgenic animals or plants.

In the present disclosure, tetracycline and a derivative thereof for the Tet-On inducible expression system comprise compounds similar to tetracycline in structure, and it can bind to the tetracycline-dependent transactivator rtTA as described herein with an association constant Ka of at least $10^{-6}$ M; preferably, $10^{-9}$M or more. The derivative of tetracycline may be selected from, for example, doxycycline (Dox), anhydrotetracycline (Atc), chlorotetracycline, oxytetracycline, and deoxytetracycline.

In the present disclosure, the Cumate functional analog that binds to the repressor CymR and can be used in the Cumate inducible expression system, can be selected from, for example, p-ethylbenzoic acid, p-propylbenzoic acid, p-isopropylbenzoic acid, p-isobutylbenzoic acid, p-tert-butylbenzoic acid, p-n-dimethylaminobenzoic acid, p-n-ethylaminobenzoic acid, and other Cumate functional analogs such as those described in U.S. Pat. No. 7,745,592.

The host cell into which the vector containing the co-regulatory sequence of tetracycline and Cumate of the present disclosure can be introduced can be, in principle, any cell, such as bacteria, fungi, animal cells or plant cells. On the other hand, the co-regulatory sequence of tetracycline and Cumate of the present disclosure can also be used in virus vectors. For example, the nucleic acid fragment contained in a prepared virus vector may contain the co-regulatory sequence of tetracycline and Cumate of the present disclosure, which may be present as a deoxyribonucleic acid in DNA virus vectors (such as adenovirus, adeno-associated virus), and may be present as a ribonucleic acid in RNA virus vectors (such as retrovirus).

As will be appreciated by those skilled in the art, there is no particular limitation on the nucleic acid fragment of interest whose transcription is controlled by the regulatory nucleic acid sequence of the present disclosure, as long as its transcription may be controlled by the regulatory nucleic acid sequence of the present disclosure.

In one aspect, the disclosure provides the following:

Item 1. A nucleic acid sequence, comprising at least 2 copies of TetO-operator sequences capable of binding to a transactivator rtTA regulatable by tetracycline or a derivative thereof, and 1 copy of a minimal promoter sequence containing a TATA box sequence, and at least 1 copy of a CuO-operator sequence capable of binding to a transcription repressor CymR regulatable by cumate, wherein the CuO-operator sequence is downstream of the 3' end of the TATA box sequence, and is 10 bp to 100 bp apart from the TATA box.

Item 2. The nucleic acid sequence of item 1, wherein the CuO-operator sequence is 30 bp to 50 bp apart from the TATA box.

Item 3. The nucleic acid sequence of item 1, wherein the CuO-operator sequence is 50 bp apart from the TATA box.

Item 4. The nucleic acid sequence of item 1, wherein the TetO-operator sequence is set forth in SEQ ID NO: 24, and/or the minimal promoter sequence is set forth in SEQ ID NO: 25 or SEQ ID NO: 26, and/or the CuO-operator sequence is set forth in SEQ ID NO:27.

Item 5. The nucleic acid sequence of item 4, wherein the nucleic acid sequence is set forth in SEQ ID NO:23, SEQ ID NO:28, SEQ ID NO:29 or SEQ ID NO:30.

Item 6. The nucleic acid sequence of any one of items 1 to 5, further comprising a spliceable intron sequence at the 3' end thereof.

Item 7. A vector comprising the nucleic acid sequence of any one of items 1 to 6.

Item 8. The vector of item 7, wherein the vector is an expression vector comprising a nucleic acid fragment of interest downstream of the 3' end of the nucleic acid sequence of any one of items 1 to 6, and the transcription of the nucleic acid fragment of interest is controlled by the nucleic acid sequence of any one of items 1 to 6.

Item 9. A host cell comprising the nucleic acid sequence of any one of items 1 to 6 or the vector of item 7 or 8.

Item 10. A method for inducing the expression of a nucleic acid fragment of interest in a host cell, comprising the following steps:

(1) introducing the vector of item 8 and a coding sequence of rtTA and a coding sequence of CymR into the host cell;

(2) expressing rtTA and CymR in the host cell subjected to step (1); and (3) providing tetracycline or a derivative thereof and cumate or a functional analog thereof for the host cell subjected to step (2).

Item 11. The method of item 10, wherein the rtTA is $rtTA_{adv}$ or $rtTA_{3G}$.

Item 12. The method of item 10, wherein the coding sequence of rtTA is set forth in SEQ ID NO: 18.

Item 13. The method of item 10, wherein the coding sequence of CymR is set forth in SEQ ID NO: 15.

BRIEF DESCRIPTION OF THE DRAWINGS

FIG. 1A shows respective RLU values of the Luciferase detection experiment corresponding to adding only DOX inducer and adding both DOX and Cumate inducer; FIG. 1B shows the ratio of the RLU value of adding Cumate and without adding Cumate inducer.

FIG. 2A shows the RLU value of Luciferase detection experiment with/without DOX and Cumate inducers; FIG. 2B shows the ratio of RLU value with/without DOX and Cumate inducers.

FIG. 3A shows the RLU value of Luciferase detection experiment with/without DOX and Cumate inducers; FIG. 3B shows the ratio of RLU value with/without DOX and Cumate inducers.

DETAILED DESCRIPTION OF THE DISCLOSURE

Figure 1:
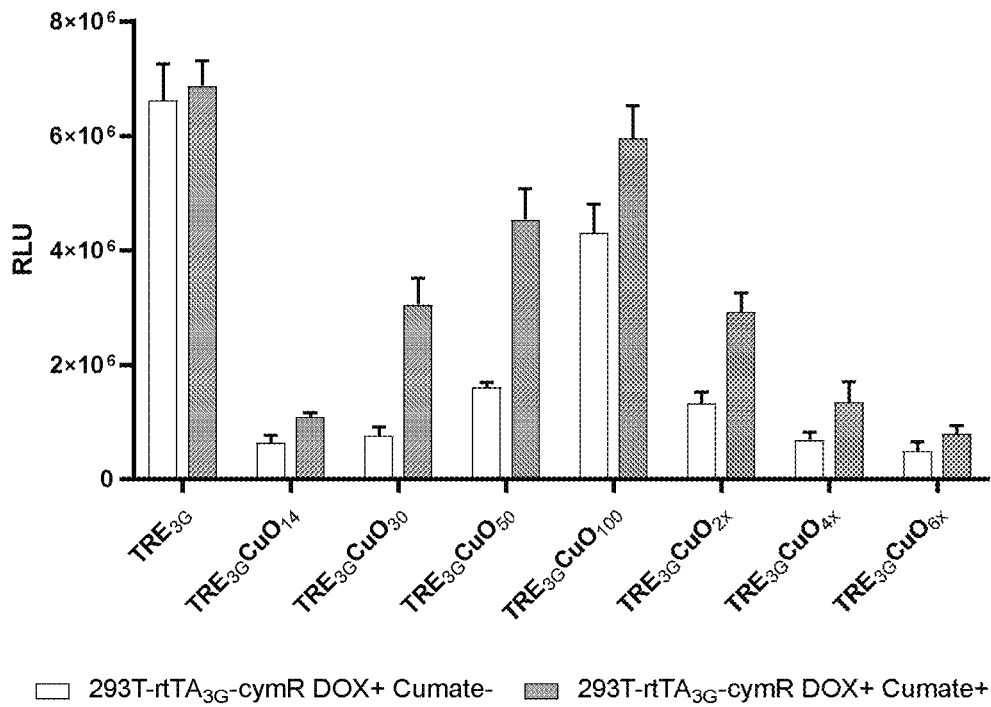
FIGS. 1A-1B show the effect of the position and quantity of the CuO operator in the complex response element in Example 2 on the induced expression level and non-induced leaky expression level of the nucleic acid fragment of interest.
Figure 1:
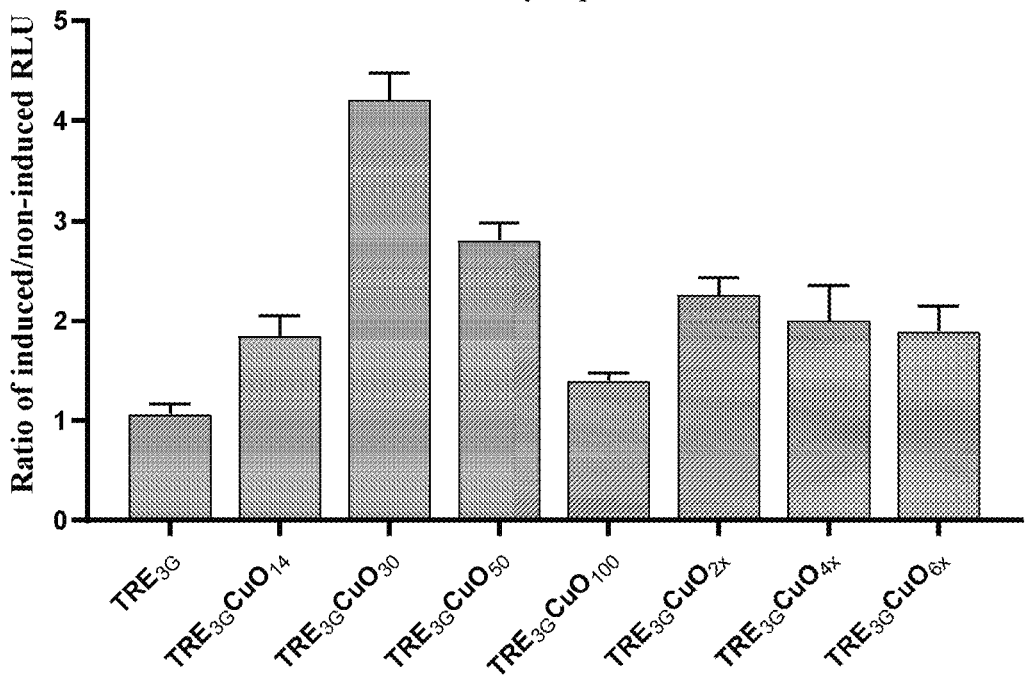

The following examples are provided to illustrate the technical solutions of the present disclosure and should not be construed as limiting the scope and spirit of the present disclosure.

Example 1: Methods for Constructing Plasmids

Molecular cloning techniques used in the following examples, such as PCR amplification of DNA fragments, restriction enzyme digestion of DNA fragments, gel recovery of DNA fragments, T4 DNA ligase ligation of two or more DNA fragments, transformation of ligation-competent cells, plasmid miniprep and identification, are all well known in the art. The following reagents are involved in the examples below: PCR enzyme (Thermo, F-530S); restriction enzyme (NEB); T4 DNA ligase (Invitrogen, 15224041); DNA fragment gel recovery kit (Omega, D2500-02); plasmid mini kit (TIANGEN, DP 105-03); competent cells (XL-10 Gold, Hu Nanfenghui Biotech Co., Ltd., JZ 011); the nucleic acid sequences set forth in SEQ ID NO: 1 to SEQ ID NO: 22 were synthesized by GenScript and used in the construction of the plasmids of the present disclosure, and the plasmid sequencing and identification were performed by Invitrogen. Table 1 shows the primers information for plasmid construction; Table 2 shows the element composition of the sequences SEQ ID NO: 1 to SEQ ID NO: 31; Table 3 is a description of the functional elements in the plasmids; Table 4 shows the numbers and corresponding names of the plasmids constructed according to the present disclosure. The sequence information of elements adopted by each plasmid involved in the following examples is an example to carry out the present disclosure, and those skilled in the art can expect that the effect of the present disclosure can be achieved by replacing the sequence of element in the plasmid used in the examples below with other sequences of element having similar biological functions, including but not limited to backbone sequences (such as replication origin, resistance genes, etc.), restriction site sequences, transposon repeat sequences, response element sequences of inducible system, insulator sequences, promoter sequences, intron sequences, polyadenylation signal (PolyA) sequences, different codon-optimized gene sequences, mutants of the above sequences of functional elements and gene sequences, and the cloning positions, cloning sequences and cloning directions of the sequences of functional elements and gene sequences. The specific methods for constructing plasmids are as follows:

1. Construction of plasmid 18BF007: the synthetic sequence SEQ ID NO: 2 (2900 bp) was digested with NotI and AsiSI, and ligated to NotI and AsiSI restriction sites of plasmid 18BF003 (SEQ ID NO: 1), respectively, to construct plasmid 18BF007.

2. Construction of plasmid 18BF011: the 18BF007 plasmid was digested by MluI and SphI; and a fragment of 1730 bp was recovered by gel and ligated to MluI and SphI restriction sites of plasmid 18BF003, to construct a plasmid 18BF011.

3. Construction of plasmid 18BF210: the synthetic sequence SEQ ID NO: 3 (1208 bp) was digested with SpeI and AgeI, and ligated to AvrII and AgeI restriction sites of plasmid 18BF011, respectively, to construct a plasmid 18BF210.

4. Construction of plasmids 118BF211, 18BF212, 18BF213, 18BF214, 18BF215, 18BF216, 18BF217 and 18BF218: the synthetic sequences SEQ ID NO: 4 (908 bp), SEQ ID NO:5 (880 bp), SEQ ID NO:6 (890 bp) and SEQ ID NO: 7 (845 bp) were digested with MluI and ClaI, and ligated to MluI and ClaI restriction sites of plasmid 18BF210, respectively, to construct plasmids 18BF212, 18BF211, 18BF214 and 18BF213, respectively. Plasmids 18BF211, 18BF212, 18BF213 and 18BF214 were digested with BstBI, and fragments of 3932 bp (18BF211), 3960 bp (18BF212), 3897 bp (18BF213) and 3942 bp (18BF214) were recovered by gel and ligated with T4 ligase to construct plasmids 18BF215, 18BF216, 18BF217 and 18BF218, respectively.

5. Construction of plasmids 18BF229, 18BF232, 18BF233, 18BF234, 18BF235, 18BF236, 18BF237, 18BF240 and 18BF241: the Luciferase gene fragment (1728 bp) was PCR-amplified by using pGL3-Basic (Promega, E1751) as a template and using Luc-F (SEQ ID NO: 32) and Luc-R (SEQ ID NO: 33) as primers, then was digested with BamHI and XhoI, and ligated to BamHI and XhoI restriction sites of plasmids 18BF210, 18BF217, 18BF218, 18BF215, 18BF216, 18BF211, 18BF212, 18BF213 and 18BF214, respectively, to construct plasmids 18BF229, 18BF232, 18BF233, 18BF234, 18BF235, 18BF236, 18BF237, 18BF240 and 18BF241.

6. Construction of plasmids 18BF251, 18BF252, 18BF253, 18BF254, 18BF255, 18BF256 and 18BF257: the synthetic sequences SEQ ID NO:8 (414 bp), SEQ ID NO:9 (414 bp), SEQ ID NO:10 (415 bp), SEQ ID NO:11 (472 bp), SEQ ID NO:12 (588 bp), SEQ ID NO:13 (704 bp) and SEQ ID NO:22 (376 bp) were digested with MluI and ClaI, and ligated to MluI and ClaI restriction sites of plasmid 18BF235, respectively, to construct plasmids 18BF251, 18BF252, 18BF253, 18BF254, 18BF255, 18BF256 and 18BF257, respectively.

7. Construction of plasmids 18BF261, 18BF262, 18BF263 and 18BF264: a BGI (C&R) intron sequence (1036 bp) was PCR-amplified by using SEQ ID NO: 17 as a template and using BGI (C&R)-F (SEQ ID NO:34) and BGI (C&R)-R (SEQ ID NO:35) as primers; an Intron (EF-1a) intron sequence (962 bp) was PCR-amplified by using pEF1alpha-IRES-AcGFP1 (Clontech) as a template and using Intron(EF-1a)-F(SEQ ID NO:36) and Intron(EF-1a)-R(SEQ ID NO: 37) as primers; an Intron (pSI) intron sequence (152 bp) was PCR-amplified by using pSI (Promega #E1721) plasmid as a template and using Intron (pSI)-F (SEQ ID NO: 38) and Intron (pSI)-R (SEQ ID NO: 39) as primers; and the above three PCR products were respectively digested with ClaI and BamHI, and then ligated to ClaI and BamHI restriction sites of plasmid 18BF235, thereby to construct plasmids 18BF261, 18BF263 and 18BF264. The synthetic SEQ ID NO: 14 (210 bp) was digested with ClaI and BamHI, and ligated to ClaI and BamHI restriction sites of plasmid 18BF235, to construct a plasmid 18BF262.

8. Construction of plasmids 19BF075 and 19BF074: the synthetic sequences SEQ ID NO: 15 (633 bp) and SEQ ID NO: 16: (1496 bp) were digested with the ClaI and XhoI and the SpeI and AgeI, respectively, and ligated in sequence to the ClaI and XhoI restriction sites and the AvrII and AgeI restriction sites of the plasmid 18BF007 to construct a plasmid 19BF073. The synthetic sequence SEQ ID NO: 17 (1979 bp) was digested by MluI and AgeI, and ligated to MluI and AgeI restriction sites of the 18BF007 plasmid to replace a CMV-BGI-MCS-pA sequence, and thereby constructing a plasmid 18BF008. The synthetic sequences SEQ ID NO: 18 (768 bp) and SEQ ID NO: 19 (765 bp) were respectively digested by ClaI and XhoI, and then respectively ligated to the ClaI and XhoI restriction sites of plasmid 18BF008, to construct plasmids 18BF085 and 18BF084 respectively. The plasmid 19BF073 was digested with SpeI and AgeI, and a fragment of 3821 bp was recovered by gel and respectively ligated to AvrII and AgeI restriction sites of plasmids 18BF085 and 18BF084 to construct a plasmids 19BF075 and 19BF074 respectively.

9. Construction of plasmid 18BF019: the synthetic sequences SEQ ID NO: 21 (1044 bp) and SEQ ID NO: 20 (1320 bp) were respectively digested by the BamHI and XhoI and the XhoI and BglII, and ligated to BamHI and BglII restriction sites of plasmid 18BF011 to construct a plasmid 18BF019.

10. Construction of plasmids 19BF229, 19BF235 and 19BF237: plasmids 18BF229, 18BF235 and 18BF237 were digested with MluI and AgeI, and fragments of 4605 bp (18BF229), 3847 bp (18BF235) and 4341 bp (18BF237) was recovered by gel and respectively ligated to MluI and AgeI restriction sites of plasmid 18BF007, to construct plasmids 19BF229, 19BF235 and 19BF237 respectively.

TABLE 1

Information for Primers

| SEQ ID NO: | Primer Name | Primer Sequence (5'-3') |
|---|---|---|
| 32 | Luc-F | TCAGGATCCATCTGCGATCTAAGTAAGCTTG |
| 33 | Luc-R | TCAACTCGAGCTAGAATTACACGGCGATC |
| 34 | BGI(C&R)-F | GTCAATCGATGGAGTCGCTGCGCGCTG |
| 35 | BGI(C&R)-R | GTCGGATCCCTGTAGGAAAAAGAAGAAGG |
| 36 | Intron(EF-1a)-F | GTCAATCGATGTAAGTGCCGTGTGTG |
| 37 | Intron(EF-1a)-R | GTCGGATCCCTGAAATGGAAGAAAAAAACT |
| 38 | Intron(pSI)-F | GTCAATCGATGTAAGTATCAAGGTTACAAG |
| 39 | Intron(pSI)-R | GTCGGATCCCTGTGGAGAGAAAGGC |

TABLE 2

Description of the appendix sequence elements

| SEQ ID NO | Description of sequence elements |
|---|---|
| SEQ ID NO: 1 | 18BF003_pma-MCS plasmid sequence (1893 bp) |
| SEQ ID NO: 2 | NotI-IR/DR-HS4I-CMV-BGI-MCS-hGHpA-HS4I-IR/DR-AsiSI (2900 bp) |
| SEQ ID NO: 3 | SpeI-SV40p-EGFP-SV40pA-AgeI (1208 bp) |
| SEQ ID NO: 4 | MluI-TRE$_{3G}$CuO-BGI-ClaI (908 bp) |
| SEQ ID NO: 5 | MluI-TRE$_{3G}$-BGI-ClaI (880 bp) |
| SEQ ID NO: 6 | MluI-TRE$_{adv}$CuO$_{52}$-BGI-ClaI (890 bp) |
| SEQ ID NO: 7 | MluI-TRE$_{adv}$-BGI-ClaI (845 bp) |
| SEQ ID NO: 8 | MluI-TRE$_{3G}$CuO$_{14}$-ClaI (414 bp) |
| SEQ ID NO: 9 | MluI-TRE$_{3G}$CuO$_{30}$-ClaI (414 bp) |
| SEQ ID NO: 10 | MluI-TRE$_{3G}$CuO$_{100}$-ClaI (415 bp) |
| SEQ ID NO: 11 | MluI-TRE$_{3G}$CuO$_{2x}$-ClaI (472 bp) |
| SEQ ID NO: 12 | MluI-TRE$_{3G}$CuO$_{4x}$-ClaI (588 bp) |
| SEQ ID NO: 13 | MluI-TRE$_{3G}$CuO$_{6x}$-ClaI (704 bp) |
| SEQ ID NO: 14 | CaII-Intron(mP1)-BamHI(210 bp) |
| SEQ ID NO: 15 | ClaI-optiCymR-XhoI (633 bp) |
| SEQ ID NO: 16 | SpeI-SV40p- optiHygroR-SV40pA-AgeI(1496 bp) |
| SEQ ID NO: 17 | MluI-CAGGS-BGI(C&R)-MCS-SV40pA-AgeI (1979 bp) |
| SEQ ID NO: 18 | ClaI-optirtTA$_{3G}$-XhoI (768 bp) |
| SEQ ID NO: 19 | ClaI-rtTA$_{adv}$-XhoI (765 bp) |
| SEQ ID NO: 20 | XhoI-ires-ECFP-BglII(1320 bp) |
| SEQ ID NO: 21 | BamHI-optiSB-XhoI (1044 bp) |
| SEQ ID NO: 22 | MluI-TRE$_{adv}$CuO$_{32}$-BGI-ClaI (376 bp) |
| SEQ ID NO: 23 | TRE$_{3G}$CuO$_{50}$ response element sequence |
| SEQ ID NO: 24 | TetO operator sequence |
| SEQ ID NO: 25 | minimal promoter sequence #1 |
| SEQ ID NO: 26 | minimal promoter sequence #2 |
| SEQ ID NO: 27 | CuO operator sequence |
| SEQ ID NO: 28 | TRE$_{3G}$CuO$_{30}$ response element sequence |
| SEQ ID NO: 29 | TRE$_{adv}$CuO$_{32}$ response element sequence |
| SEQ ID NO: 30 | TRE$_{adv}$CuO$_{52}$ response element sequence |
| SEQ ID NO: 31 | sequence of human β-globulin intron (BGI) |

TABLE 3

Description of functional elements of plasmids

| Element name | Description of functions |
|---|---|
| IR/DR(L/R) | inverted repeat (IR) and direct repeat (DR) of SB transposon system |
| HS4I | 4 core isolator of chicken beta-globulin highly sensitive position |
| HygroR | codon optimized sequence encoding hygromycin resistance gene |
| Sleeping Beauty (optiSB) | codon-optimized gene sequence encoding Sleeping Beauty (SB) transposase (SEQ ID NO: 21) |
| BGI | human β-globulin intron (SEQ ID NO: 31) |
| CMV | strong expression promoter of human cytomegalovirus |
| MCS | multiple cloning site of restriction enzyme |
| CAGGS | chimeric promoter of cytomegalovirus promoter enhancer part and chicken β-actin promoter |
| BGI (C&R) | chimeric intron of chicken β-actin and rabbit β-globulin |
| Intron (mP1) | Mouse Prm1 gene intron (7-202 bp in SEQ ID NO: 14, which is consistent with 942-1137 bp in Accession number of FJ411376) |

TABLE 3-continued

Description of functional elements of plasmids

| Element name | Description of functions |
| --- | --- |
| Intron (EF-1a) | EF-1α intron of pEF1alpha-IRES-AcGFP1(Clontech) plasmid |
| Intron (pSI) | chimera intron of human beta globin and immunoglobulin heavy chain gene in pSI (Promega#E1721) plasmid |
| $TRE_{3G}CuO/$ $TRE_{3G}CuO_{50}$ | response element of Tet-On (based on 7xTetO sequence in $TRE_{3G}$) and Cumate complex inducible expression system designed in the present disclosure, wherein the CuO sequence is spaced 50 bp behind the TATA box (SEQ ID NO: 23) |
| $TRE_{3G}CuO_{14}$ | response element of Tet-On (based on 7xTetO sequence in $TRE_{3G}$) and Cumate complex inducible expression system designed in the present disclosure, wherein the CuO sequence is spaced 14 bp behind the TATA box (10-317 bp in SEQ ID NO: 8) |
| $TRE_{3G}CuO_{30}$ | response element of Tet-On (based on 7xTetO sequence in $TRE_{3G}$) and Cumate complex inducible expression system designed in the present disclosure, wherein the CuO sequence is spaced 30 bp behind the TATA box (SEQ ID NO: 28) |
| $TRE_{3G}CuO_{100}$ | response element of Tet-On (based on 7xTetO sequence in $TRE_{3G}$) and Cumate complex inducible expression system designed in the present disclosure, wherein the CuO sequence is spaced 100 bp behind the TATA box (10-403 bp in SEQ ID NO: 10) |
| $TRE_{3G}CuO_{2x}$ | response element of Tet-On (based on 7xTetO sequence in $TRE_{3G}$) and Cumate complex inducible expression system designed in the present disclosure, wherein the two repeated CuO sequence is spaced 50 bp behind the TATA box (10-411 bp in SEQ ID NO: 11) |
| $TRE_{3G}CuO_{4x}$ | response element of Tet-On (based on 7xTetO sequence in $TRE_{3G}$) and Cumate complex inducible expression system designed in the present disclosure, wherein the 4 repeated CuO sequence is spaced 50 bp behind the TATA box (10-527 bp in SEQ ID NO: 12) |
| $TRE_{3G}CuO_{6x}$ | response element of Tet-On (based on 7xTetO sequence in $TRE_{3G}$) and Cumate complex inducible expression system designed in the present disclosure, wherein the 6 repeated CuO sequence is spaced 50 bp behind the TATA box (10-643 bp in SEQ ID NO: 13) |
| $TRE_{adv}CuO/TRE_{-adv}CuO_{52}$ | response element of Tet-On (based on 7xTetO sequence in $TRE_{adv}$) and Cumate complex inducible expression system designed in the present disclosure, wherein the CuO sequence is spaced 52 bp behind the TATA box (SEQ ID NO: 30) |
| $TRE_{adv}CuO_{32}$ | response element of Tet-On (based on 7xTetO sequence in $TRE_{adv}$) and Cumate complex inducible expression system designed in the present disclosure, wherein the CuO sequence is spaced 32 bp behind the TATA box (SEQ ID NO: 29) |
| $TRE_{3G}/TRE_{adv}$ | response element of Tet-On inducible expression system: $TRE_{3G}$ is the third generation of response element/$TRE_{adv}$ is the second generation of response element (SEQ ID NO: 5/SEQ ID NO: 7) |
| SV40p | Simian vacuolar virus 40 promoter |
| IRES | ribosome entry site |
| EGFP | gene sequence encoding green fluorescent protein |
| ECFP | Gene sequence encoding cyan fluorescent protein |
| Luciferase (Luc) | Gene sequence encoding luciferase |
| polyA (hGHpA/SV40pA) | polyadenylation sequence of transcription terminator (hGHpA human growth factor terminator/SV40pA simian vacuolar virus 40 terminator) |
| optiCymR | codon-optimized coding sequence for repressor CymR protein of Cumate-induced expression system (13-621 bp in SEQ ID NO: 15) |
| $rtTA_{3G}$ | codon-optimized gene sequence encoding the third generation of $rtTA_{3G}$ transactivation element of Tet-On regulatory system (13-756 bp in SEQ ID NO: 18) |
| $rtTA_{adv}$ | gene sequence encoding the second generation of $rtTA_{adv}$ transactivation element of Tet-On regulatory system (13-756 bp in SEQ ID NO: 19) |

TABLE 4

Plasmid numbers and names

| Plasmid Number | Plasmid Name |
| --- | --- |
| 18BF003 | pma-MCS |
| 18BF007 | pmaSBT3-2xHS4I-CMV-BGI-MCS |
| 18BF011 | pmaCMV-BGI-MCS |
| 18BF210 | pmaCMV-BGI-MCS-SV40p-EGFP |
| 18BF211 | pma$TRE_{3G}$-BGI-MCS-SV40p-EGFP |
| 18BF212 | pma$TRE_{3G}CuO_{50}$-BGI-MCS-SV40p-EGFP |
| 18BF213 | pma$TRE_{adv}$-BGI-MCS-SV40p-EGFP |
| 18BF214 | pma$TRE_{adv}CuO_{52}$-BGI-MCS-SV40p-EGFP |
| 18BF215 | pma$TRE_{3G}$-MCS-SV40p-EGFP |
| 18BF216 | pma$TRE_{3G}CuO_{50}$-MCS-SV40p-EGFP |
| 18BF217 | pma$TRE_{adv}$-MCS-SV40p-EGFP |
| 18BF218 | pma$TRE_{adv}CuO_{52}$-MCS-SV40p-EGFP |
| 18BF229 | pmaCMV-BGI-Luciferase-SV40p-EGFP |
| 18BF232 | pma$TRE_{adv}$-Luciferase-SV40p-EGFP |
| 18BF233 | pma$TRE_{adv}CuO_{52}$-Luciferase-SV40p-EGFP |
| 18BF234 | pma$TRE_{3G}$-Luciferase-SV40p-EGFP |

TABLE 4-continued

Plasmid numbers and names

| Plasmid Number | Plasmid Name |
|---|---|
| 18BF235 | pmaTRE$_{3G}$CuO$_{50}$-Luciferase-SV40p-EGFP |
| 18BF236 | pmaTRE$_{3G}$-BGI-Luciferase-SV40p-EGFP |
| 18BF237 | pmaTRE$_{3G}$CuO$_{50}$-BGI-Luciferase-SV40p-EGFP |
| 18BF240 | pmaTRE$_{adv}$-BGI-Luciferase-SV40p-EGFP |
| 18BF241 | pmaTRE$_{adv}$CuO$_{52}$-BGI-Luciferase-SV40p-EGFP |
| 18BF251 | pmaTRE$_{3G}$CuO$_{14}$-Luciferase-SV40p-EGFP |
| 18BF252 | pmaTRE$_{3G}$CuO$_{30}$-Luciferase-SV40p-EGFP |
| 18BF253 | pmaTRE$_{3G}$CuO$_{100}$-Luciferase-SV40p-EGFP |
| 18BF254 | pmaTRE$_{3G}$CuO$_{2x}$-Luciferase-SV40p-EGFP |
| 18BF255 | pmaTRE$_{3G}$CuO$_{4x}$-Luciferase-SV40p-EGFP |
| 18BF256 | pmaTRE$_{3G}$CuO$_{6x}$-Luciferase-SV40p-EGFP |
| 18BF257 | pmaTRE$_{adv}$CuO$_{32}$-Luciferase-SV40p-EGFP |
| 18BF261 | pmaTRE$_{3G}$CuO-BGI(C&R)-Luciferase-SV40p-EGFP |
| 18BF262 | pmaTRE$_{3G}$CuO-Intron(mP1)-Luciferase-SV40p-EGFP |
| 18BF263 | pmaTRE$_{3G}$CuO-Intron(EF-1a)-Luciferase-SV40p-EGFP |
| 18BF264 | pmaTRE$_{3G}$CuO-Intron(pSI)-Luciferase- SV40p-EGFP |
| 19BF073 | pmaSBT3-2xHS4I-CMV-BGI-optiCymR-HygroR |
| 18BF008 | pmaSBT3-2xHS4I-CAGGS-BGI (C&R)-MCS |
| 18BF085 | pmaSBT3-2xHS4I-CAGGS-BGI (C&R)-optirtTA$_{3G}$ |
| 18BF084 | pmaSBT3-2xHS4I-CAGGS-BGI (C&R)-rtTA$_{adv}$ |
| 19BF075 | pmaSBT3-2xHS4I-CAGGS-BGI (C&R)-optirtTA$_{3G}$-CMV-BGI-optiCymR-HygroR |
| 19BF074 | pmaSBT3-2xHS4I-CAGGS-BGI (C&R)-rtTA$_{adv}$-CMV-BGI-optiCymR-HygroR |
| 18BF019 | pmaCMV-BGI-optiSB-IRES-ECFP |
| 19BF229 | pmaSBT3-2xHS4I-CMV-BGI-Luciferase-SV40p-EGFP |
| 19BF235 | pmaSBT3-2xHS4I-TRE$_{3G}$CUO-Luciferase-SV40p-EGFP |
| 19BF237 | pmaSBT3-2xHS4I-TRE$_{3G}$CUO-BGI-Luciferase-SV40p-EGFP |

Example 2: The Effect of the Position and Number of CuO Operator on the Induced Expression Level and Non-Induced Leaky Expression Level The experiment described in the present Example is to study and verify the effect of the position and copy number of the CuO operator in the Tet-On and Cumate complex response element on the induced expression level and non-induced leaky expression level of the complex response element, and to optimize and confirm the optimal position and copy number of the CuO operator. In the present Example, based on the 7×TetO sequence in the TRE$_{3G}$ response element and the minimal promoter sequence #1 (SEQ ID NO: 25), the response elements TRE$_{3G}$CuO$_{14}$ (10-317 bp in SEQ ID NO: 8), TRE$_{3G}$CuO$_{30}$ (SEQ ID NO: 28), TRE$_{3G}$CuO$_{50}$ (SEQ ID NO: 23) and TRE$_{3G}$CuO$_{100}$ (10-403 bp in SEQ ID NO: 10) were designed by linking a CuO operator sequence at 10 bp to 100 bp downstream of the TATA box (at 14 bp, 30 bp, 50 bp and 100 bp downstream of the TATA box, respectively), and a Luciferase reporter gene sequence was linked downstream of the 3' end of the above response elements, to construct plasmids 18BF251, 18BF252, 18BF235 and 18BF253. Further, in order to study the effect of multiple copies of CuO operators, 2, 4 and 6 copies of CuO operator sequences were respectively inserted at 50 bp downstream of the TATA box, to design the response elements TRE$_{3G}$CuO$_{2x}$ (10-411 bp in SEQ ID NO: 11), TRE$_{3G}$CuO$_{4x}$ (10-527 bp in SEQ ID NO: 12) and TRE$_{3G}$CuO$_{6x}$ (10-643 bp in SEQ ID NO: 13), and then a Luciferase reporter gene sequence was linked downstream of 3' end of the above response elements to construct plasmids 18BF254, 18BF255 and 18BF256. In 293T-rtTA$_{3G}$-CymR cells stably expressing rtTA$_{3G}$ and CymR genes, the above plasmids were transiently transfected, and the optimal position and number of CuO operator were validated by measuring the luciferase fluorescence value of samples added with both DOX and Cumate inducers and that of the control added with the DOX inducer only. The specific experimental methods were as follows:

1. Construction of 293T-rtTA$_{adv}$-CymR and 293T-rtTA$_{3G}$-CymR Cells with SB Transposon System 293T cells were seeded at 1.5E+06 cells per 60 mm culture dish, and cultured in DMEM (Sigam, D6429) complete medium supplemented with 10% FBS (ExCell, 11H116) at 37° C. and 5% CO 2. After 24 hours of culture, transfection was carried out according to the PEI method. During transfection, 500 µL of transfection reagent which contained 5.5 ug of total plasmid was added to each 60 mm culture dish, and the mass ratio of total plasmid to PEI MAX (Polysciences, 24765-1) was 1:4. The transfection was carried out according to the PEI method, wherein the amount of total plasmid was 5.5 µg. The transfection was performed with plasmids 19BF074:18BF019 at a molar ratio of 10:1 to obtain 293T-rtTA$_{adv}$-CymR cells; and the transfection was performed with plasmids 19BF075:18BF019 at a molar ratio of 10:1 to obtain 293T-rtTA$_{3G}$-CymR cells. The plasmid and PEI MAX were mixed uniformly, and then put into a culture dish after standing for 15 minutes. 3 hours after transfection, the medium was changed to a complete DMEM medium, and the transfection operation was completed. After 24 hours of transfection, the cells were digested with trypsin and all seeded in a 100 mm culture dish (Corning, 430167), and 200 µg/ml of hygromycin (Sangon Biotech A600230-0001) drug screening was performed for at least three passages. After the growth of cells under the pressure of drug screening was consistent with that of the original 293T cells, the following experiments were performed.

2. Detection of the Performance of Each Response Element Under Both DOX and Cumate Induction or Under DOX Induction Alone by Luciferase Fluorescence Intensity Assay The 293T-rtTA$_{3G}$-CymR cells were seeded in a 96-well plate (Corning 3916) at 2.5E+04 cells per well, and the medium was 100 microliters of DMEM complete medium. After 24 hours of culture, the following plasmids were transfected according to the PEI method: 18BF234 (TRE$_{3G}$), 18BF251 (TRE$_{3G}$CuO$_{14}$), 18BF252 (TRE$_{3G}$CuO$_{30}$), 18BF235 (TRE$_{3G}$CuO$_{50}$), 18BF253 (TRE$_{3G}$CuO$_{100}$), 18BF254 (TRE$_{3G}$CuO$_{2x}$), 18BF255 (TRE$_{3G}$CuO$_{4x}$) and 18BF256 (TRE$_{3G}$CuO$_{6x}$); 10 μL of transfection reagent was added into each well during transfection, which contains 0.3 ug of total plasmids including 0.01 ug of the above 8 kinds of plasmids to be tested and 0.29 ug of 18BF003 empty plasmid. The mass ratio of total plasmid to PEI MAX (Polysciences, 24765-1) was 1:4, and each plasmid was transfected into 6 wells. After 3 hours of transfection, the complete DMEM medium was changed; and the inducer 1 ug/ml DOX (doxycycline hydrochloride, Sangon Biotech (Shanghai), A600889)) and 200 ug/ml Cumate (Aladdin, I107765) were added into 3 wells; and 1 ug/ml DOX alone was added into the remaining 3 wells. After 24 hours of transfection, relative light unit RLU of each well was detected using a Steady-Gb® Luciferase Assay System (Promega, E2610) kit according to the instruction (Promega, FB037), wherein the detection instrument was a fluorescence microplate reader (Perkin Elmer Victor V).

The results were shown in FIG. 1: the induced expression level of response element in the Tet-On inducible expression system was affected by the CuO operator sequence; the closer the distance between the CuO operator and the TATA box of TRE response element was, the lower the expression level after induction was. However, as the distance between the CuO operator and the TATA box increases, the leaky expression level of non-Cumate induction became higher. Based on the results of the expression level after induction, the leaky expression level of non-Cumate induction and the ratio of Cumate induced/leaky expression level, it was determined that the optimal distance between the CuO and the TATA box was 30 bp to 50 bp, and the induced expression level was 3.06E+06 RLU and 4.53E+06 RLU, which was respectively 44.5% and 66.0% of the induced expression level of TRE$_{3G}$ response element; and the ratio of induced/leaky expression level based on Cumate inducible expression system was 4.21 times and 2.81 times that of TRE$_{3G}$ response element, respectively. The expression level after induction was further decreased by increasing the copy number of CuO operator to 2, 4 or 6, and the ratio of Cumate induced/leaky expression level was not increased. Based on the above results, it is the optimal condition to insert the CuO operator and insert only one copy at a distance of 30 bp to 50 bp from the TATA box of the TRE response element.

Based on the 7×TetO sequence in the TRE$_{adv}$ response element and the minimal promoter sequence #2 (SEQ ID NO: 26), the response elements TRE$_{adv}$CuO$_{32}$ (SEQ ID NO:29) and TRE$_{adv}$CuO$_{52}$ (SEQ ID NO:30) were designed by linking a CuO operator at 32 bp and 52 bp downstream of the TATA box, and a Luciferase reporter gene sequence was linked downstream of the 3' end of the above response elements, to construct plasmids 18BF257 and 18BF233. By the same method as above, the detected induced expression levels were 3.26+06 RLU and 4.88E+06 RLU, respectively, which were 37.8% and 53.4% of the induced expression level for TRE$_{adv}$ response element; the ratio of induced/leaky expression level based on Cuamte inducible expression system was 4.97 times and 3.23 times that for the TRE$_{adv}$ response element, respectively. In the subsequent examples, experiments were performed with response elements TRE$_{adv}$CuO$_{52}$ and TRE$_{3G}$CuO$_{50}$, and they were marked as TRE$_{adv}$CuO and TRE$_{3G}$CuO response elements, respectively.

Example 3: The Effect of Single Regulation/Complex Regulation and Introns on the Induced Expression Level and Non-Induced Leaky Expression Level In Tet-On inducible expression system, the induced transcription activity and the leaky transcription activity were comprehensively affected by the TetO operator linking sequence of the TRE response element and the minimal promoter sequence, as well as different mutants of the transactivator rtTA. In addition, the transport and stability of messenger ribonucleic acid may be enhanced by linking a spliceable intron sequence downstream of the 3' end of the response element and upstream of the 5' end of the regulated nucleic acid fragment of interest, but the induced transcription activity and leaky transcription activity of response element of the inducible expression system may also be affected. Based on this, the optimal design scheme of complex response element was determined in this Example based on the induced expression level and the ratio of induced/leaky expression level of Luciferase gene under the combination of the following conditions: (1) Tet-On and Cumate complex response elements TRE$_{adv}$CuO and TRE$_{3G}$CuO designed based on the TRE$_{adv}$ and TRE$_{3G}$ response element sequences; (2) whether an intron was linked; (3) being regulated by the transactivator rtTA$_{adv}$ or rtTA$_{3G}$. A total of 8 design schemes were compared in this Example: TRE$_{adv}$ (18BF232), TRE$_{adv}$CuO (18BF233), TRE$_{3G}$ (18BF234), TRE$_{3G}$CuO (18BF235), TRE$_{adv}$-BGI (18BF240, wherein the response element was TRE$_{adv}$, and a human β-globulin intron was linked between the 3' end of the response element and the 5' end of the Luciferase gene), TRE$_{adv}$CuO-BGI (18BF241, wherein the response element was TRE$_{adv}$CuO, and a human β-globulin intron was linked between the 3' end of the response element and the 5' end of the Luciferase gene), TRE$_{3G}$-BGI (18BF236, wherein the response element was TRE$_{3G}$, and a human β-globulin intron was linked between the 3' end of the response element and the 5' end of the Luciferase gene) and TRE$_{3G}$CuO-BGI (18BF237, wherein the response element was TRE$_{3G}$CuO, and a human β-globulin intron was linked between the 3' end of the response element and the 5' end of the Luciferase gene). The promoter CMV-BGI (18BF229, wherein the promoter was CMV, and a human β-globulin intron was linked between the 3' end of the CMV promoter and the 5' end of the Luciferase gene) was used as a positive control. In 293T-rtTA$_{adv}$-CymR cells stably expressing rtTA$_{adv}$ and CymR genes and 293T-rtTA$_{3G}$-CymR cells stably expressing rtTA$_{3G}$ and CymR genes, the above plasmids were transiently transfected, and the optimal combination of complex response elements was verified by measuring the luciferase fluorescence value of samples added with both DOX and Cumate inducers and that of the control added with no inducer. The specific experimental methods were as follows:

The 293T-rtTA$_{adv}$-CymR and 293T-rtTA$_{3G}$-CymR cells constructed in Example 2 were seeded into a 96-well plate (Corning 3916) at 2.5E+04 cells per well, and the medium was 100 microliters of DMEM complete medium. After 24 hours of culture, the above 9 plasmids were transfected according to the PEI method. 10 μL of transfection reagent, which contains 0.3 ug of total plasmids including 0.01 ug of the above 9 plasmids to be tested and 0.29 μg of 18BF003 empty plasmid, was added into each well during transfection. The mass ratio of total plasmid to PEI MAX (Polysciences, 24765-1) was 1:4, and each plasmid was transfected into 6 wells for 293T-rtTA$_{adv}$-CymR and 293T- rtTA$_{3G}$-CymR cells respectively. After 3 hours of transfection, the DMEM complete medium was replaced; the inducer 1 ug/ml DOX and 200 ug/ml Cumate were added into 3 wells for each cell; and the same amount of medium was added into the remaining 3 wells as a control. After 24 hours of transfection, relative light unit RLU of each well was detected using a Steady-Gb® Luciferase Assay System (Promega, E2610) kit according to the instructions (Promega, FB037), wherein the detection instrument was a fluorescence microplate reader (Perkin Elmer Victor V).

Figure 2:
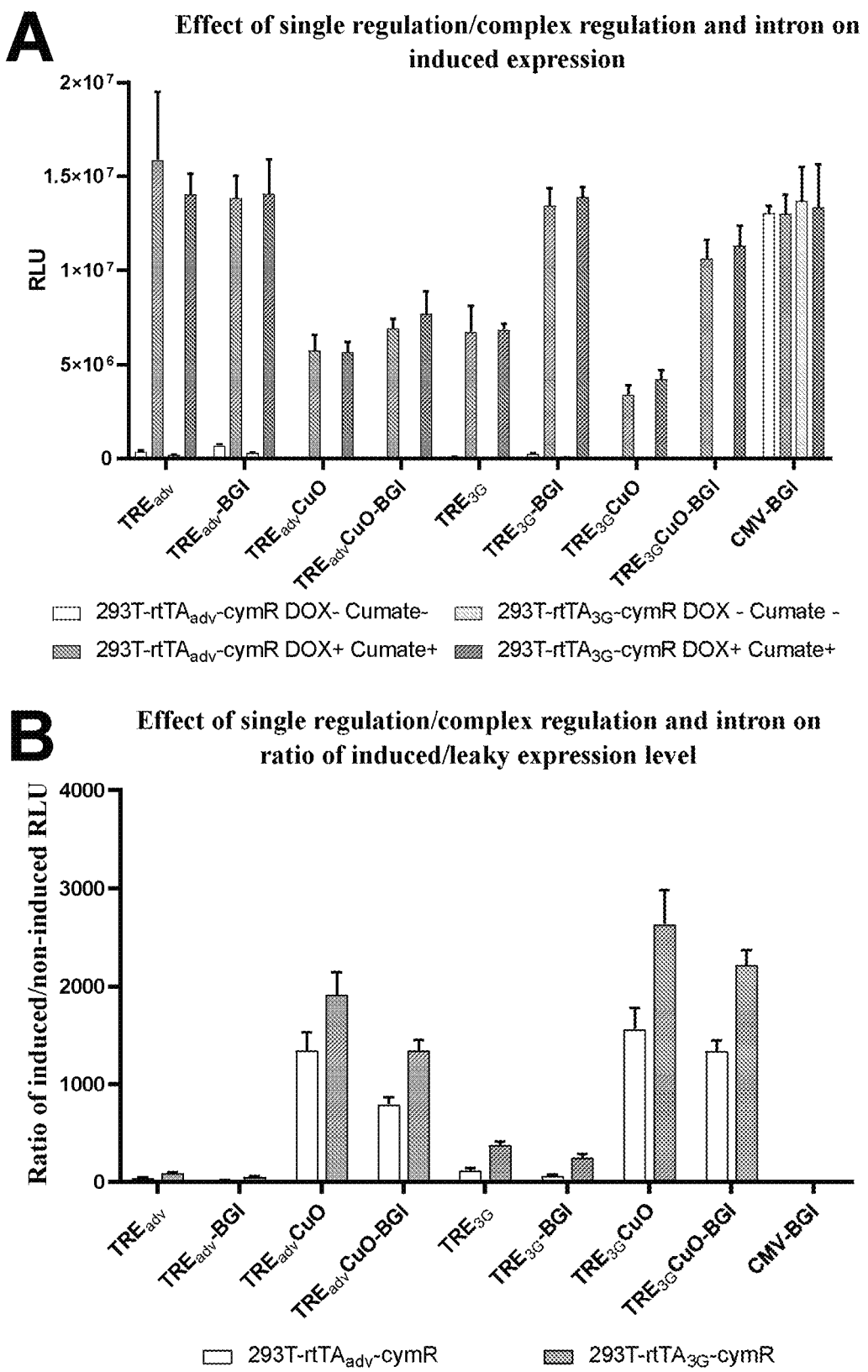
FIGS. 2A-2B show the effects of the single regulatory response element, the complex regulatory response element, and the introns linked downstream of the response element in Example 3 on the induced expression level and the non-induced leaky expression level of the nucleic acid fragment of interest.

The experimental results were shown in FIG. 2: (1) Compared with the TRE single regulatory response element, the TRECuO complex response element significantly increases the ratio of induced/leaky expression level by one to two orders of magnitude. Compared with the TRE$_{adv}$CuO complex response element, the TRE$_{3G}$CuO complex response element can better control the leaky expression. In 293T-rtTA$_{adv}$-CymR cells, the induced/leaky expression ratios of TRE$_{3G}$CuO and TRE$_{adv}$CuO were 1565 and 1345 times, respectively, which showed an increase of 16.4%; in 293T-rtTA$_{3G}$-CymR cells, the induced/leaky expression ratios of TRE$_{3G}$CuO and TRE$_{adv}$CuO were respectively 2635 and 1915 times, which showed an increase of 37.6%. However, compared with the TRE single regulatory response element, the TRECuO complex response element significantly decreased the induced expression level. In 293T-rtTA$_{adv}$-CymR cells, the induced expression levels of TRE$_{3G}$CuO and TRE$_{adv}$CuO were 50.4% and 36.3% of those of the corresponding TRE$_{3G}$ and TRE$_{adv}$ single regulatory response elements, respectively; in 293T-rtTA$_{3G}$-CymR cells, the induced expression levels of TRE$_{3G}$CuO and TRE$_{adv}$CuO were 61.8% and 40.3% of those of the single regulatory response element, respectively. (2) In terms of induced expression level, the TRE$_{3G}$CuO complex response element was more sensitive to the downstream intron than the TRE$_{adv}$CuO complex response element, and the induced expression level in the presence of the intron BGI was significantly increased. In 293T-rtTA$_{adv}$-CymR cells, the induced expression levels of TRE$_{3G}$CuO and TRE$_{3G}$CuO-BGI were 3.4E+06 RLU and 10.6E+06 RLU, respectively, which were 50.4% and 157.9% of the induced expression level of TRE$_{3G}$, and linking an intron can increase the induced expression level of TRE$_{3G}$CuO complex response element by 2.13 times; in 293T-rtTA$_{3G}$-CymR cells, the induced expression levels of TRE$_{3G}$CuO and TRE$_{3G}$CuO-BGI were 4.24E+06 and 11.3E+06, which were 61.8% and 165.0% of the induced expression level of TRE$_{3G}$, respectively, and linking an intron can increase the induced expression level of TRE$_{3G}$CuO complex response element by 1.67 times. (3) Regarding the induced expression level, there was no significant difference between the transactivator rtTA$_{3G}$ and rtTA$_{adv}$ in the 8 design schemes, but rtTA$_{3G}$ had a significant advantage regarding the ratio of induced/leaky expression levels. The average ratio of induced/leaky expression level of rtTA$_{3G}$ in 8 design schemes was 1110 times, which was 1.68 times that of rtTA$_{adv}$ (the average ratio of induced/leaky expression level of rtTA$_{adv}$ was 661 times).

Based on the above results, the TRE$_{3G}$CuO complex response element has a better ability to control the leaky expression as compared to TRE$_{adv}$ and TRE$_{3G}$ and TRE$_{adv}$CuO complex response elements; with linking the intron BGI downstream, the TRE$_{3G}$CuO complex response element can maintain the control of the leaky expression while greatly improving the induced expression level. Under the regulation of rtTA$_{3G}$, the induced expression level of TRE$_{3G}$CuO-BGI was 80.6% of that of TRE$_{adv}$, 80.5% of that of TRE$_{adv}$-BGI, 199.9% of that of TRE$_{adv}$CuO, 147.0% of that of TRE$_{adv}$CuO-BGI, 165.0% of that of TRE$_{3G}$, 81.5% of that of TRE$_{3G}$-BGI and 267.2% of that of TRE$_{3G}$CuO, reaching 84.7% of that of the constitutive promoter CMV-BGI; the ratio of induced/non-induced expression level of TRE$_{3G}$CuO-BGI was 24.5 times that of TRE$_{adv}$, 43.4 times that of TRE$_{adv}$-BGI, 1.2 times that of TRE$_{adv}$CuO, 1.6 times that of TRE$_{adv}$CuO-BGI, 5.9 times that of TRE$_{3G}$, 8.9 times that of TRE$_{3G}$-BGI and 0.8 times that of TRE$_{3G}$CuO.

Example 4: The Effect of Different Introns on the Induced Expression Level and Non-Induced Leaky Expression Level of TRE$_{3G}$CuO Complex Response Element In Example 3, the linkage of the intron BGI significantly increased the induced transcription activity of the TRE$_{3G}$CuO complex induction response element and the expression level of the target gene of Luciferase. It was verified in this Example whether other introns had similar effects. In this example, the introns in the four commonly used plasmid vectors were cloned between the 3'downstream of the TRE$_{3G}$CuO complex response element and the 5'upstream of the luciferase reporter gene, to construct plasmids 18BF261, 18BF262, 18BF263 and 18BF264 respectively containing BGI (C&R), Intron (mP1), Intron (EF-1a) and Intron (pSI) introns, and the specific methods for constructing a plasmid was described in Example 1. In 293T-rtTA$_{3G}$-CymR cells stably expressing rtTA$_{3G}$ and CymR genes, the above plasmids and TRE$_{3G}$CuO (18BF235), TRE$_{3G}$CuO-BGI (18BF237) and CMV-BGI (18BF229) plasmids were transiently transfected, respectively, and the effect of each intron on the induced expression and non-induced leaky expression of the TRE$_{3G}$CuO complex response element was verified by measuring the luciferase fluorescence values of samples added with both DOX and Cumate inducers and that of the control added with no inducer. The specific experimental methods were as follows:

The 293T-rtTA$_{3G}$-CymR cells were seeded in a 96-well plate (Corning 3916) at 2.5E+04 cells per well, and the medium was 100 microliters of DMEM complete medium. After 24 hours of culture, the above 7 plasmids were respectively transfected according to the PEI method. 10 μL of transfection reagent, which contains 0.3 ug of total plasmids including 0.01 ug of the above 7 plasmids to be tested and 0.29 μg of 18BF003 empty plasmid, was added into each well during transfection. The mass ratio of total plasmid to PEI MAX (Polysciences, 24765-1) was 1:4, and each plasmid was transfected into 6 wells. After 3 hours of transfection, the DMEM complete medium was replaced; the inducer 1 ug/ml DOX and 200 ug/ml Cumate were added into 3 wells; and the same amount of medium was added into the remaining 3 wells. After 24 hours of transfection, relative light unit RLU of each well was detected using a Steady-Gb® Luciferase Assay System (Promega, E2610) kit according to the instructions (Promega, FB037), wherein the detection instrument was a fluorescence microplate reader (Perkin Elmer Victor V).

Figure 3:
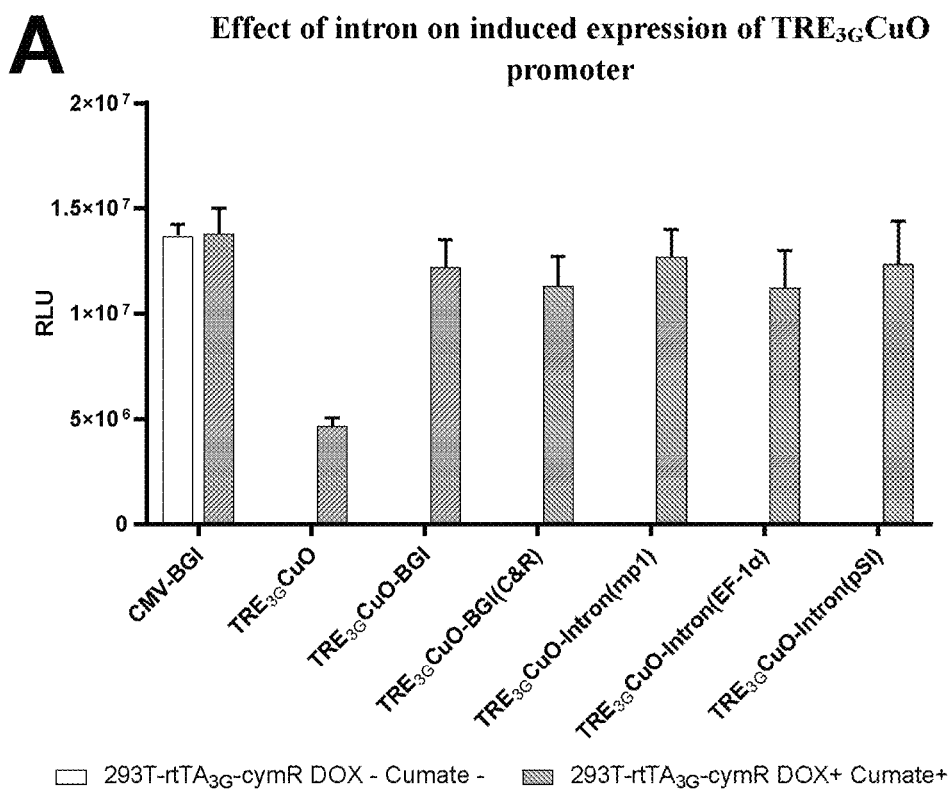
FIGS. 3A-3B show the effects of different introns in Example 4 on the induced expression level and non-induced leaky expression level of $TRE_{3G}CuO$ complex response element.
Figure 3:
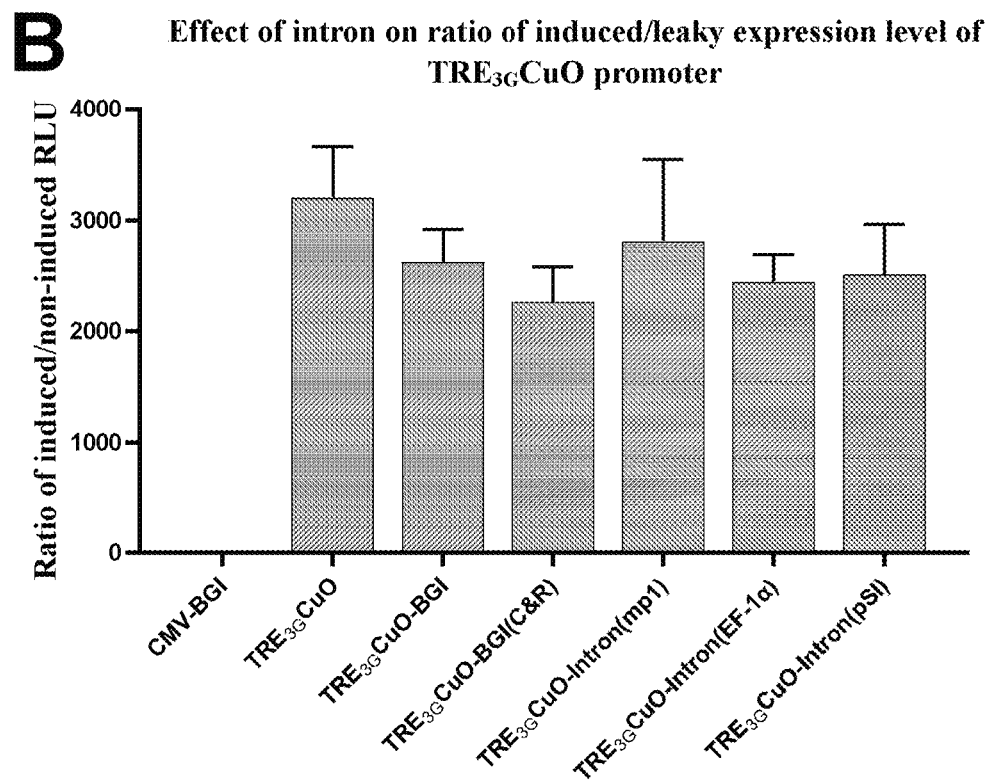

The results were shown in FIG. 3: there is no significant difference in the induced expression level and the ratio of induced/leaky expression level between plasmids 18BF261, 18BF262, 18BF263 and 18BF264 containing four other introns and the TRE$_{3G}$CuO-BGI (18BF237), all of which can achieve the effect of TRE$_{3G}$CuO-BGI as described in Example 3. In the intron, a 5'splice site, a 3'splice site, and a splice branch point are required for splicing. This Example demonstrates that spliceable introns which meet the above conditions can achieve the experimental effects as described in the present disclosure. Therefore, the effects as described in the present disclosure should not be limited by specific intron sequences, and any sequence capable of RNA splicing in mammalian cells can achieve the above functions. Intron sequences that may be selected include, but are not limited to, introns in common cloning vectors, such as a rabbit β-globulin intron, a hybrid intron derived from human β-globulin and immunoglobulin heavy chain intron, EF-1α intron A, SV40 intron, a hybrid intron derived from adenovirus and immunoglobulin heavy chain intron, a modified human cytomegalovirus intron, a hybrid intron derived from chicken β-actin (CBA) and mouse microvirus (MMV) intron, a chimera derived from chicken β-actin and rabbit β-globulin intron, and a mP1 intron; or any intron of any gene of any eukaryote; or an artificial intron sequence designed based on the intron splicing rules.

Example 5: Study of Induced Transcription Activity of the $TRE_{3G}CuO$ Complex Response Element Under Different Induction Combinations In this Example, stable cell lines, under complex regulation of Tet-ON and Cumate, $TRE_{3G}CuO$ or $TRE_{3G}CuO$-intron, and with Luciferase as the reporter gene, were constructed. Then, based on these cell lines, induced transcription activities of the reporter gene under the following 4 induction conditions were detected: without inducer, Cumate only, DOX only or both DOX and Cumate inducers. In this Example, the Luciferase reporter gene was taken as an example, and in principle, the method of the present disclosure was not affected by the nucleic acid fragment of interest. The specific experimental methods were as follows:

1. Construction of a Luciferase Stable Cell Line Regulated by DOX and Cumate by Using SB Transposon System:

293T cells were seeded at 1.5E+06 cells per 60 mm culture dish, and cultured in DMEM (Sigam, D6429) complete medium supplemented with 10% FBS (ExCell, 11H116) at 37° C. and 5% CO 2. After 24 hours of culture, transfection was carried out according to the PEI method. During transfection, 500 µL of transfection reagent which contained 5.5 ug of total plasmid was added to each 60 mm culture dish, and the mass ratio of total plasmid to PEI MAX (Polysciences, 24765-1) was 1:4; and thereby 3 Luciferase stable cell lines were constructed. The transfection plasmids were transfected at the 19BF075:19BF229:18BF019 molar ratio of 5:5:1 to obtain 293T(T&C)-CMV-BGI-Luc cells; the transfection plasmids were transfected at the 19BF075:19BF235:18BF019 molar ratio of 5:5:1 to obtain 293T(T&C)-$TRE_{3G}CuO$-Luc cells; the transfection plasmids were transfected at the 19BF075:19BF237:18BF019 molar ratio of 5:5:1 to obtain 293T(T&C)-$TRE_{3G}CuO$-BGI-Luc cells. The plasmid and PEI MAX were mixed uniformly, and then put into a culture dish after standing for 15 minutes. 3 hours after transfection, the medium was changed to a complete DMEM medium, and the transfection operation was completed. After 24 hours of transfection, the cells were digested with trypsin and all seeded in a 100 mm culture dish (Corning, 430167), and 200 µg/ml of hygromycin (Sangon Biotech A600230-0001) drug screening was performed for at least three passages. After the growth of cells under the pressure of drug screening was consistent with that of the original 293T cells, the above 3 cells were diluted to 1 cell per well by a limiting dilution method and seeded in a 96-well plate; when the cells grew to about 50% of the bottom area of the well, the wells with strong EGFP green fluorescence intensity and uniform luminescence were selected under the fluorescence microscope, and 3 independent clones of each cell were selected for the following experiments.

2. Induction of Luciferase Expression by Using Different Combinations of DOX and Cumate:

For the above 3 cells, 3 independent clones for each cell were seeded into a 96-well plate (Corning 3916) at 2.5E+04 cells per well, with 8 wells per clone, and the medium was 100 microliters of DMEM complete medium. After 24 hours of culture, the medium was replaced and the following reagents were added into the duplicate wells of the 8 wells for each cell: (1) the same amount of medium, (2) Cumate at a final concentration of 200 ug/ml, (3) DOX at a final concentration of 1 ug/ml, or (4) DOX at a final concentration of 1 ug/ml and Cumate at a final concentration of 200 ug/ml. After 24 hours of further culture, relative light unit RLU of each well was detected using a Steady-Glo® Luciferase Assay System (Promega, E2610) kit according to the instruction (Promega, FB037), wherein the detection instrument was a fluorescence microplate reader (Perkin Elmer Victor V).

Figure 4:
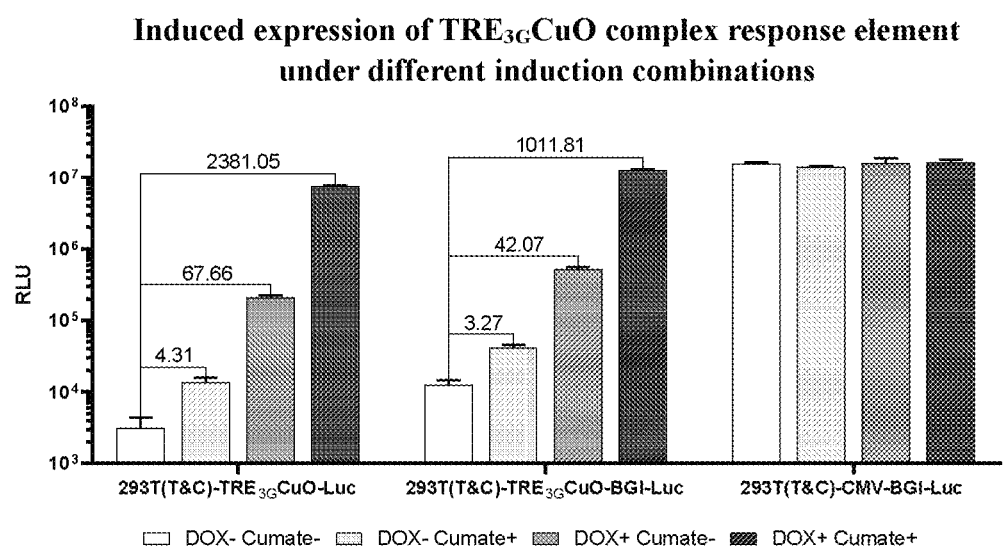
FIG. 4 shows the respective induced transcription activities of the nucleic acid fragment of interest regulated by $TRE_{3G}CuO$ and $TRE_{3G}CuO$-BGI in Example 5 under different combinations of induction. The ordinate shows the RLU value of the Luciferase detection experiment with different inducers; the 4-color histogram shows the four combinations of inducers; the numbers on the horizontal line represent the ratio of RLU value under the induction condition and the non-induction condition (white).

The experimental results were shown in FIG. 4: under the condition of only adding Cumate, the induced transcription activities of $TRE_{3G}CuO$ and $TRE_{3G}CuO$-BGI were 1.36E+04 RLU and 4.16E+04 RLU, which were respectively 4.31 times and 3.27 times higher than those obtained by no induction. Under the condition of only adding DOX, the induced transcription activities of $TRE_{3G}CuO$ and $TRE_{3G}CuO$-BGI were 2.14E+05 RLU and 5.34E+05 RLU, which were respectively 67.66 times and 42.07 times higher than those obtained by no induction, and were 15.71 times and 12.86 times higher than those obtained under the induction condition of only adding Cumate. Under the condition of adding both DOX and Cumate, the induced transcription activities of $TRE_{3G}CuO$ and $TRE_{3G}CuO$-BGI were 7.54E+06 RLU and 1.29E+07 RLU, which were respectively 2381.05 times and 1011.81 times higher than those obtained by no induction; were 552.99 times and 309.27 times higher than those obtained under the induction condition of only adding Cumate; were 35.19 times and 24.05 times higher than those obtained under the induction condition of only adding DOX. Based on the above results, $TRE_{3G}CuO$ and $TRE_{3G}CuO$-BGI complex response elements can regulate the induced transcription activity of the nucleic acid fragment of interest at various levels according to different combinations of inducers, with ranges of 4.31 times to 2381.05 times and 3.27 times to 1011.81 times, respectively; when both DOX and Cumate inducers were added, the maximum induced transcription activities can reach 47.84% and 81.54% of that of CMV promoter, respectively. With further optimization of the concentration of DOX and/or Cumate inducer, the transcription activity of the nucleic acid fragment of interest can be further finely regulated at different transcription activity levels.

What is claimed is:

1. A nucleic acid sequence, comprising at least 2 copies of Tet operator (TetO) sequences capable of binding to a reverse tetracycline controlled transactivator (rtTA) regulatable by tetracycline or a derivative thereof, 1 copy of a minimal promoter sequence containing a TATA box sequence, and at least 1 copy of a Cumate operator (CuO) sequence capable of binding to a transcription repressor cysteine metabolism repressor (CymR) regulatable by cumate, wherein the CuO-sequence is downstream of the 3' end of the TATA box sequence, and is 30 bp to 50 bp apart from the TATA box.

2. The nucleic acid sequence of claim 1, wherein the CuO-sequence is about 50 bp apart from the TATA box.

3. The nucleic acid sequence of claim 1, wherein the TetO-sequence is as set forth in SEQ ID NO: 24.

4. A vector comprising the nucleic acid sequence of claim 3.

5. The nucleic acid sequence of claim 1, wherein the nucleic acid sequence is set forth in SEQ ID NO:23, SEQ ID NO:28, SEQ ID NO:29 or SEQ ID NO:30.

6. A vector comprising the nucleic acid sequence of claim 5.

7. The nucleic acid sequence of claim 1, further comprising a spliceable intron sequence at the 3' end thereof.

8. A vector comprising the nucleic acid sequence of claim 1.

9. The vector of claim 8, wherein the vector is an expression vector comprising a nucleic acid fragment downstream of the 3' end of the nucleic acid sequence, and the transcription of the nucleic acid fragment is controlled by the nucleic acid sequence.

10. A cultured host cell comprising the vector of claim 8.

11. The nucleic acid sequence of claim 1, wherein the minimal promoter sequence is set forth in SEQ ID NO: 25 or SEQ ID NO: 26.

12. A vector comprising the nucleic acid sequence of claim 11.

13. The nucleic acid sequence of claim 1, wherein the CuO-operator sequence is set forth in SEQ ID NO:27.

14. A vector comprising the nucleic acid sequence of claim 13.

15. A cultured host cell comprising the nucleic acid sequence of claim 1.

16. A method for inducing the expression of a nucleic acid fragment in a host cell, comprising the following steps:
   (1) introducing the vector of claim 9, a sequence comprising a coding sequence of reverse tetracycline controlled transactivator (rtTA) and a sequence comprising a coding sequence of cysteine metabolism repressor (CymR) into the host cell;
   (2) expressing rtTA and CymR in the host cell subjected to step (1); and
   (3) providing tetracycline or a derivative thereof and cumate or a functional analog thereof for the host cell subjected to step (2).

17. The method of claim 16, wherein the rtTA is rtTA of Tet-On Advanced Inducible Gene Expression Systems (rtTA$_{adv}$) or rtTA of Tet-On 3G Inducible Expression Systems (rtTA$_{3G}$).

18. The method of claim 16, wherein the sequence comprising the coding sequence of rtTA is set forth in SEQ ID NO: 18.

19. The method of claim 16, wherein the sequence comprising the coding sequence of CymR is set forth in SEQ ID NO: 15.

20. The method of claim 16, wherein the sequence comprising the coding sequence of rtTA and the sequence comprising the coding sequence of CymR are on a single vector or on different vectors.

* * * * *

UNITED STATES PATENT AND TRADEMARK OFFICE
CERTIFICATE OF CORRECTION

| | | |
|---|---|---|
| PATENT NO. | : 11,680,267 B2 | Page 1 of 1 |
| APPLICATION NO. | : 17/766685 | |
| DATED | : June 20, 2023 | |
| INVENTOR(S) | : Bofu Xue et al. | |

It is certified that error appears in the above-identified patent and that said Letters Patent is hereby corrected as shown below:

On the Title Page

Item [71], delete "Guandong" and insert -- Guangdong --

Signed and Sealed this
Third Day of October, 2023

Katherine Kelly Vidal
*Director of the United States Patent and Trademark Office*

SEQUENCE LISTING

<160> NUMBER OF SEQ ID NOS: 39

<210> SEQ ID NO 1
<211> LENGTH: 1893
<212> TYPE: DNA
<213> ORGANISM: Artificial sequence
<220> FEATURE:
<223> OTHER INFORMATION: 18BF003_pma-MCS plasmid sequence

<400> SEQUENCE: 1

```
actgcggccg ccctgcaggt caactagtga cgtcttaatt aattgccggc tggaacgcgt      60
ttcgaacatc gattgaattc tggccaagtg gatccgctag ctctagagtc gacggtacca     120
agcttgcctc gagccatgga gatctgcatg ccctaggtcc ggaaccggtt ggcgcgccat     180
ctggcagcga tcgccgcgga acccctattt gtttattttt ctaaatacat tcaaatatgt     240
atccgctcat gagacaataa ccctgataaa tgcttcaata atattgaaaa aggaagagta     300
tgagtattca catttccgt gtcgccctta ttcccttttt tgcggcattt tgccttcctg      360
ttttgctca cccagaaacg ctggtgaaag taaaagatgc tgaagatcag ttgggtgcac      420
gagtgggtta tcgaactg gatctcaaca gcggtaagat ccttgagagt tttcgccccg       480
aagaacgttt tccaatgatg agcacttta aagttctgct atgtggcgcg gtattatccc      540
gtattgacgc cgggcaagag caactcggtc gccgcataca ctattctcag aatgacttgg     600
ttgagtactc accagtcaca gaaaagcatc ttacggatgg catgacagta agagaattat     660
gcagtgctgc cataaccatg agtgataaca ctgcggccaa cttacttctg acaacgatcg     720
gaggaccgaa ggagctaacc gcttttttgc acaacatggg ggatcatgta actcgccttg     780
atcgttggga accggagctg aatgaagcca taccaaacga cgagcgtgac accacgatgc     840
ctgtagcaat ggcaacaacg ttgcgcaaac tattaactgg cgaactactt actctagctt     900
cccggcaaca attaatagac tggatggagg cggataaagt tgcaggacca cttctgcgct     960
cggcccttcc ggctggctgg tttattgctg ataaatctgg agccggtgag cgtgggtctc    1020
gcggtatcat tgcagcactg gggccagatg gtaagccctc ccgtatcgta gttatctaca    1080
cgacggggag tcaggcaact atggatgaac gaaatagaca gatcgctgag ataggtgcct    1140
cactgattaa gcattggtaa cgtacggaag ttagagaaaa ggcataagta gaaaagatca    1200
aaggatcttc ttgagatcct ttttttctgc gcgtaatctg ctgcttgcaa acaaaaaaac    1260
caccgctacc agcggtggtt tgtttgccgg atcaagagct accaactctt tttccgaagg    1320
taactggctt cagcagagcg cagataccaa atactgttct tctagtgtag ccgtagttag    1380
gccaccactt caagaactct gtagcaccgc ctacatacct cgctctgcta atcctgttac    1440
cagtggctgc tgccagtggc gataagtcgt gtcttaccgg gttggactca agacgatagt    1500
taccggataa ggcgcagcgg tcgggctgaa cggggggttc gtgcacacag cccagcttgg    1560
agcgaacgac ctacaccgaa ctgagatacc tacagcgtga gctatgagaa agcgccacgc    1620
ttcccgaagg gagaaaggcg gacaggtatc cggtaagcgg cagggtcgga acaggagagc    1680
gcacgaggga gcttccaggg ggaaacgcct ggtatcttta tagtcctgtc gggtttcgcc    1740
acctctgact tgagcgtcga tttttgtgat gctcgtcagg gggcggagc ctatggaaaa     1800
acgccagcaa cgcggccttt ttacggttcc tggccttttg ctggcctttt gctcatctca    1860
tgaaaattat gcaaattgag ccagtcaggc agt                                 1893
```

<210> SEQ ID NO 2
<211> LENGTH: 2900

<212> TYPE: DNA
<213> ORGANISM: Artificial sequence
<220> FEATURE:
<223> OTHER INFORMATION: NotI-IR/DR-HS4I-CMV-BGI-MCS-hGHpA-HS4I-IR/DR-AsiSI sequence

<400> SEQUENCE: 2

| | | | | | |
|---|---|---|---|---|---|
| gcggccgcat | ctatacagtt | gaagtcggaa | gtttacatac | acttaagttg | gagtcattaa | 60 |
| aactcgtttt | tcaactactc | cacaaatttc | ttgttaacaa | acaatagttt | tggcaagtca | 120 |
| gttaggacat | ctactttgtg | catgacacaa | gtcattttc | caacaattgt | ttacagacag | 180 |
| attatttcac | ttataattca | ctgtatcaca | attccagtgg | gtcagaagtt | tacatacact | 240 |
| aagttgactg | tgcctttaaa | cagcttggaa | aattccagaa | aatgatgtca | tggctttagc | 300 |
| ctgcagggag | ggacagcccc | cccccaaagc | ccccagggat | gtaattacgt | ccctcccccg | 360 |
| ctaggggca | gcagcgagcc | gcccggggct | ccgctccggt | ccggcgctcc | ccccgcatcc | 420 |
| ccgagccggc | agcgtgcggg | gacagcccgg | gcacggggaa | ggtggcacgg | gatcgctttc | 480 |
| ctctgaacgc | ttctcgctgc | tctttgagcc | tgcagacacc | tggggggata | cggggaaaag | 540 |
| gacctgcagg | tcaactagtg | acgtcttaat | taattgccgg | ctggacgtac | gcgtctagtt | 600 |
| attaatagta | atcaattacg | gggtcattag | ttcatagccc | atatatggag | ttccgcgtta | 660 |
| cataacttac | ggtaaatggc | ccgcctggct | gaccgcccaa | cgacccccgc | ccattgacgt | 720 |
| caataatgac | gtatgttccc | atagtaacgc | caatagggac | tttccattga | cgtcaatggg | 780 |
| tggagtattt | acggtaaact | gcccacttgg | cagtacatca | agtgtatcat | atgccaagta | 840 |
| cgccccctat | tgacgtcaat | gacggtaaat | ggcccgcctg | gcattatgcc | cagtacatga | 900 |
| ccttatggga | ctttcctact | tggcagtaca | tctacgtatt | agtcatcgct | attaccatgg | 960 |
| tgatgcggtt | ttggcagtac | atcaatgggc | gtggatagcg | gtttgactca | cggggatttc | 1020 |
| caagtctcca | ccccattgac | gtcaatggga | gtttgttttg | gcaccaaaat | caacgggact | 1080 |
| ttccaaaatg | tcgtaacaac | tccgccccat | tgacgcaaat | gggcggtagg | cgtgtacggt | 1140 |
| gggaggtcta | tataagcaga | gctcgtttag | tgaaccgtca | gatcgcctgg | agacgccatc | 1200 |
| cacgctgttt | tgacctccat | agaagacacc | gggaccgatc | cagcctccgc | ggattcgaat | 1260 |
| cccggccggg | aacggtgcat | tggaacgcgg | attccccgtg | ccaagagtga | cgtaagtacc | 1320 |
| gcctatagag | tctataggcc | cacaaaaaat | gctttcttct | tttaatatac | ttttttgttt | 1380 |
| atcttatttc | taatactttc | cctaatctct | ttctttcagg | gcaataatga | tacaatgtat | 1440 |
| catgcctctt | tgcaccattc | taaagaataa | cagtgataat | ttctgggtta | aggcaatagc | 1500 |
| aatatttctg | catataaata | tttctgcata | taaattgtaa | ctgatgtaag | aggtttcata | 1560 |
| ttgctaatag | cagctacaat | ccagctacca | ttctgctttt | attttatggt | tgggataagg | 1620 |
| ctggattatt | ctgagtccaa | gctaggccct | tttgctaatc | atgttcatac | ctcttatctt | 1680 |
| cctcccacag | ctcctgggca | acgtgctggt | ctgtgtgctg | gcccatcact | ttggcaaaga | 1740 |
| attgggattc | gaacatcgat | tgaattctgg | ccaggatccg | ctagctctag | agtcgacggt | 1800 |
| accagtacta | agcttgcctc | gagccatgga | gatctacggg | tggcatccct | gtgacccctc | 1860 |
| cccagtgcct | ctcctggccc | tggaagttgc | cactccagtg | cccaccagcc | ttgtcctaat | 1920 |
| aaaattaagt | tgcatcattt | tgtctgacta | ggtgtccttc | tataatatta | tggggtggag | 1980 |
| gggggtggta | tggagcaagg | ggcaagttgg | gaagacaacc | tgtagggcct | gcggggtcta | 2040 |
| ttgggaacca | agctggagtg | cagtggcaca | atcttggctc | actgcaatct | ccgcctcctg | 2100 |
| ggttcaagcg | attctcctgc | ctcagcctcc | cgagttgttg | ggattccagg | caagcatgac | 2160 |

```
caggctcagc taattttttgt ttttttggta gagacggggt ttcaccatat tggccaggct    2220
ggtctccaac tcctaatctc aggtgatcta cccaccttgg cctcccaaat tgctgggatt    2280
acaggcgtga accactgctc ccttccctgt ccttgcatgc cctaggcagc tgtccggaac    2340
cggtgtttaa acaggccttt tccccgtatc ccccaggtg tctgcaggct caaagagcag    2400
cgagaagcgt tcagaggaaa gcgatcccgt gccaccttcc ccgtgccgg gctgtccccg    2460 cacgctgccg gctcggggat gcgggggag cgccggaccg gagcggagcc ccgggcggct    2520
cgctgctgcc ccctagcggg ggagggacgt aattacatcc ctgggggctt tggggggggg    2580 ctgtcccctca ggccttggcg cgccctaaag ccatgacatc attttctgga attttccaag    2640
ctgtttaaag gcacagtcaa cttagtgtat gtaaacttct gacccactgg aattgtgata    2700
cagtgaatta aagtgaaat aatctgtctg taaacaattg ttggaaaaat gacttgtgtc    2760
atgcacaaag tagatgtcct aactgacttg ccaaaactat tgtttgttaa caagaaattt    2820
gtggagtagt tgaaaaacga gttttaatga ctccaactta agtgtatgta aacttccgac    2880
ttcaactgta tagcgatcgc                                                2900

<210> SEQ ID NO 3
<211> LENGTH: 1208
<212> TYPE: DNA
<213> ORGANISM: Artificial sequence
<220> FEATURE:
<223> OTHER INFORMATION: SpeI-SV40p-EGFP-SV40pA-AgeI sequence

<400> SEQUENCE: 3
actagtgtgt gtcagttagg gtgtggaaag tccccaggct ccccagcagg cagaagtatg      60
caaagcatgc atctcaatta gtcagcaacc aggtgtggaa agtccccagg ctccccagca     120
ggcagaagta tgcaaagcat gcatctcaat tagtcagcaa ccatagtccc gcccctaact     180
ccgcccatcc cgcccctaac tccgcccagt tccgcccatt ctccgcccca tggctgacta     240
atttttttta tttatgcaga ggccgaggcc gcctctgcct ctgagctatt ccagaagtag     300
tgaggaggct ttttggagg ccataggctt ttgcaaaaag ctatggtgag caagggcgag     360
gagctgttca ccggggtggt gcccatcctg gtcgagctgg acggcgacgt aaacggccac     420
aagttcagcg tgtccggcga gggcgagggc gatgccacct acggcaagct gaccctgaag     480
ttcatctgca ccaccggcaa gctgcccgtg ccctggccca cctcgtgac cacccctgacc     540 tacggcgtgc agtgcttcag ccgctacccc gaccacatga agcagcacga cttcttcaag     600
tccgccatgc ccgaaggcta cgtccaggag cgcaccatct tcttcaagga cgacggcaac     660
tacaagaccc gcgccgaggt gaagttcgag ggcgacaccc tggtgaaccg catcgagctg     720
aagggcatcg acttcaagga ggacggcaac atcctgggc acaagctgga gtacaactac     780
aacagccaca acgtctatat catggccgac aagcagaaga cggcatcaa ggtgaacttc     840 aagatccgcc acaacatcga ggacggcagc gtgcagctcg ccgaccacta ccagcagaac     900
acccccatcg gcgacggccc cgtgctgctg cccgacaacc actacctgag cacccagtcc     960
gccctgagca agacccccaa cgagaagcgc gatcacatgg tcctgctgga gttcgtgacc    1020
gccgccggga tcactctcgg catggacgag ctgtacaagt aaaacttgtt tattgcagct    1080
tataatggtt acaaataaag caatagcatc acaaatttca caataaagc attttttttca    1140 ctgcattcta gttgtggttt gtccaaactc atcaatgtat cttacctagg cagctgtccg    1200
gaaccggt                                                            1208
```

<210> SEQ ID NO 4
<211> LENGTH: 908
<212> TYPE: DNA
<213> ORGANISM: Artificial sequence
<220> FEATURE:
<223> OTHER INFORMATION: MluI-TRE3GCuO-BGI-ClaI sequence

<400> SEQUENCE: 4

```
acgcgttact cccctatcagt gatagagaac gtatgaagag tttactccct atcagtgata      60
gagaacgtat gcagacttta ctccctatca gtgatagaga acgtataagg agtttactcc     120
ctatcagtga tagagaacgt atgaccagtt tactccctat cagtgataga gaacgtatct     180
acagtttact cccctatcagt gatagagaac gtatatccag tttactccct atcagtgata     240
gagaacgtat taggcgtgta cggtgggcgc ctataaaagc agagctcgtt tagtgaaccg     300
tcagatcgcc tggagcaatt ccacatacaa acagaccaga ttgtctgttt gttacacttt     360
tgtcttatac caactttccg taccacttcc taccctcgta aattcgaatc ccggccggga     420
acggtgcatt ggaacgcgga ttccccgtgc caagagtgac gtaagtaccg cctatagagt     480
ctataggccc acaaaaaatg ctttcttctt taatatact tttttgttta tcttatttct     540
aatactttcc ctaatctctt tctttcaggg caataatgat acaatgtatc atgcctcttt     600
gcaccattct aaagaataac agtgataatt tctgggttaa ggcaatagca atatttctgc     660
atataaatat ttctgcatat aaattgtaac tgatgtaaga ggtttcatat tgctaatagc     720
agctacaatc cagctaccat tctgcttta tttatggtt gggataaggc tggattattc      780
tgagtccaag ctaggccctt ttgctaatca tgttcatacc tcttatcttc ctcccacagc     840
tcctgggcaa cgtgctggtc tgtgtgctgg cccatcactt tggcaaagaa ttgggattcg     900
aaatcgat                                                              908
```

<210> SEQ ID NO 5
<211> LENGTH: 880
<212> TYPE: DNA
<213> ORGANISM: Artificial sequence
<220> FEATURE:
<223> OTHER INFORMATION: MluI-TRE3G-BGI-ClaI sequence

<400> SEQUENCE: 5

```
acgcgttact cccctatcagt gatagagaac gtatgaagag tttactccct atcagtgata      60
gagaacgtat gcagacttta ctccctatca gtgatagaga acgtataagg agtttactcc     120
ctatcagtga tagagaacgt atgaccagtt tactccctat cagtgataga gaacgtatct     180
acagtttact cccctatcagt gatagagaac gtatatccag tttactccct atcagtgata     240
gagaacgtat taggcgtgta cggtgggcgc ctataaaagc agagctcgtt tagtgaaccg     300
tcagatcgcc tggagcaatt ccacaacact tttgtcttat accaactttc cgtaccactt     360
cctaccctcg taaattcgaa tcccggccgg gaacggtgca ttggaacgcg gattccccgt     420
gccaagagtg acgtaagtac cgcctataga gtctataggc ccacaaaaaa tgctttcttc     480
ttttaatata cttttttgtt tatcttattt ctaatactt ccctaatctc tttctttcag     540
ggcaataatg atacaatgta tcatgcctct ttgcaccatt ctaaagaata acagtgataa     600
tttctgggtt aaggcaatag caatatttct gcatataaat atttctgcat ataaattgta     660
actgatgtaa gaggtttcat attgctaata gcagctacaa tccagctacc attctgcttt     720
tattttatgg ttgggataag gctggattat tctgagtcca agctaggccc ttttgctaat     780
catgttcata cctcttatct tcctcccaca gctcctgggc aacgtgctgg tctgtgtgct     840
```

```
ggcccatcac tttggcaaag aattgggatt cgaaatcgat                  880
```

<210> SEQ ID NO 6
<211> LENGTH: 890
<212> TYPE: DNA
<213> ORGANISM: Artificial sequence
<220> FEATURE:
<223> OTHER INFORMATION: MluI-TREadvCuO52-BGI-ClaI sequence

<400> SEQUENCE: 6

```
acgcgtgacg aggatcgttc gagcgagttt actccctatc agtgatagag aacgtatgtc   60
gagtttactc cctatcagtg atagagaacg atgtcgagtt tactccctat cagtgataga  120
gaacgtatgt cgagtttact ccctatcagt gatagagaac gtatgtcgag tttactccct  180
atcagtgata gagaacgtat gtcgagttta tccctatcag tgatagagaa cgtatgtcga  240
gtttactccc tatcagtgat agagaacgta tgtcgaggta ggcgtgtacg gtgggaggcc  300
tatataagca accggtgttt agtgaaccgt cagatcgcct ggagacgcca tcataataca  360
aacagaccag attgtctgtt tgttttcgaa tcccggccgg aacggtgcat tggaacgcg   420
gattccccgt gccaagagtg acgtaagtac cgcctataga gtctataggc ccacaaaaaa  480
tgctttcttc ttttaatata ctttttttgtt tatcttattt ctaatacttt ccctaatctc  540
tttctttcag gcaataatg atacaatgta tcatgcctct ttgcaccatt ctaaagaata  600
acagtgataa tttctgggtt aaggcaatag caatatttct gcatataaat atttctgcat  660
ataaattgta actgatgtaa gaggtttcat attgctaata gcagctacaa tccagctacc  720
attctgcttt tattttatgg ttgggataag gctggattat tctgagtcca agctaggccc  780
ttttgctaat catgttcata cctcttatct cctcccaca gctcctgggc aacgtgctgg  840
tctgtgtgct ggcccatcac tttggcaaag aattgggatt cgaaatcgat              890
```

<210> SEQ ID NO 7
<211> LENGTH: 845
<212> TYPE: DNA
<213> ORGANISM: Artificial sequence
<220> FEATURE:
<223> OTHER INFORMATION: MluI-TREadv-BGI-ClaI sequence

<400> SEQUENCE: 7

```
acgcgtgacg aggatcgttc gagcgagttt actccctatc agtgatagag aacgtatgtc   60
gagtttactc cctatcagtg atagagaacg atgtcgagtt tactccctat cagtgataga  120
gaacgtatgt cgagtttact ccctatcagt gatagagaac gtatgtcgag tttactccct  180
atcagtgata gagaacgtat gtcgagttta tccctatcag tgatagagaa cgtatgtcga  240
gtttactccc tatcagtgat agagaacgta tgtcgaggta ggcgtgtacg gtgggaggcc  300
tatataagca gagctcgttt agtgaaccgt cagatcgcct tcgaatcccg gccgggaacg  360
gtgcattgga acgcggattc cccgtgccaa gagtgacgta agtaccgcct atagagtcta  420
taggcccaca aaaaatgctt tcttctttta atatactttt ttgtttatct tatttctaat  480
actttcccta atctctttct tcagggcaa taatgataca atgtatcatg cctctttgca  540
ccattctaaa gaataacagt gataatttct gggttaaggc aatagcaata tttctgcata  600
taaatatttc tgcatataaa ttgtaactga tgtaagaggt ttcatattgc taatagcagc  660
tacaatccag ctaccattct gcttttattt tatggttggg ataaggctgg attattctga  720
gtccaagcta ggcccttttg ctaatcatgt tcatacctct tatcttcctc ccacagctcc  780
```

```
tgggcaacgt gctggtctgt gtgctggccc atcactttgg caaagaattg ggattcgaaa      840
tcgat                                                                  845

<210> SEQ ID NO 8
<211> LENGTH: 414
<212> TYPE: DNA
<213> ORGANISM: Artificial sequence
<220> FEATURE:
<223> OTHER INFORMATION: MluI-TRE3GCuO14-ClaI sequence

<400> SEQUENCE: 8
acgcgttact ccctatcagt gatagagaac gtatgaagag tttactccct atcagtgata       60
gagaacgtat gcagacttta ctccctatca gtgatagaga acgtataagg agtttactcc      120
ctatcagtga tagagaacgt atgaccagtt tactccctat cagtgataga gaacgtatct      180
acagtttact ccctatcagt gatagagaac gtatatccag tttactccct atcagtgata      240
gagaacgtat taggcgtgta cggtgggcgc ctataaaagc agagctcgtt acaaacagac      300
cagattgtct gtttgtttta gtgaaccgtc agatcgcctg gagcaattcc acaacacttt      360
tgtcttatac caactttccg taccacttcc taccctcgta aattcgaaat cgat            414

<210> SEQ ID NO 9
<211> LENGTH: 414
<212> TYPE: DNA
<213> ORGANISM: Artificial sequence
<220> FEATURE:
<223> OTHER INFORMATION: MluI-TRE3GCuO30-ClaI sequence

<400> SEQUENCE: 9
acgcgttact ccctatcagt gatagagaac gtatgaagag tttactccct atcagtgata       60
gagaacgtat gcagacttta ctccctatca gtgatagaga acgtataagg agtttactcc      120
ctatcagtga tagagaacgt atgaccagtt tactccctat cagtgataga gaacgtatct      180
acagtttact ccctatcagt gatagagaac gtatatccag tttactccct atcagtgata      240
gagaacgtat taggcgtgta cggtgggcgc ctataaaagc agagctcgtt tagtgaaccg      300
tcagatacaa acagaccaga ttgtctgttt gtttcgcctg gagcaattcc acaacacttt      360
tgtcttatac caactttccg taccacttcc taccctcgta aattcgaaat cgat            414

<210> SEQ ID NO 10
<211> LENGTH: 415
<212> TYPE: DNA
<213> ORGANISM: Artificial sequence
<220> FEATURE:
<223> OTHER INFORMATION: MluI-TRE3GCuO100-ClaI sequence

<400> SEQUENCE: 10
acgcgttact ccctatcagt gatagagaac gtatgaagag tttactccct atcagtgata       60
gagaacgtat gcagacttta ctccctatca gtgatagaga acgtataagg agtttactcc      120
ctatcagtga tagagaacgt atgaccagtt tactccctat cagtgataga gaacgtatct      180
acagtttact ccctatcagt gatagagaac gtatatccag tttactccct atcagtgata      240
gagaacgtat taggcgtgta cggtgggcgc ctataaaagc agagctcgtt tagtgaaccg      300
tcagatcgcc tggagcaatt ccacaacact tttgtcttat accaactttc cgtaccactt      360
cctaccctcg taaaatacaa acagaccaga ttgtctgttt gttttcgaaa tcgat           415

<210> SEQ ID NO 11
<211> LENGTH: 472
```

```
<212> TYPE: DNA
<213> ORGANISM: Artificial sequence
<220> FEATURE:
<223> OTHER INFORMATION: MluI-TRE3GCuO2x-ClaI sequence

<400> SEQUENCE: 11
acgcgttact ccctatcagt gatagagaac gtatgaagag tttactccct atcagtgata        60
gagaacgtat gcagacttta ctccctatca gtgatagaga acgtataagg agtttactcc       120
ctatcagtga tagagaacgt atgaccagtt tactccctat cagtgataga gaacgtatct       180
acagtttact ccctatcagt gatagagaac gtatatccag tttactccct atcagtgata       240
gagaacgtat taggcgtgta cggtgggcgc ctataaaagc agagctcgtt tagtgaaccg       300
tcagatcgcc tggagcaatt ccacatacaa acagaccaga ttgtctgttt gttttcgata       360
ttaggatatc actccgttta aactacaaac agaccagatt gtctgtttgt tacacttttg       420
tcttatacca actttccgta ccacttccta ccctcgtaaa ttcgaaatcg at               472

<210> SEQ ID NO 12
<211> LENGTH: 588
<212> TYPE: DNA
<213> ORGANISM: Artificial sequence
<220> FEATURE:
<223> OTHER INFORMATION: MluI-TRE3GCuO4x-ClaI sequence

<400> SEQUENCE: 12
acgcgttact ccctatcagt gatagagaac gtatgaagag tttactccct atcagtgata        60
gagaacgtat gcagacttta ctccctatca gtgatagaga acgtataagg agtttactcc       120
ctatcagtga tagagaacgt atgaccagtt tactccctat cagtgataga gaacgtatct       180
acagtttact ccctatcagt gatagagaac gtatatccag tttactccct atcagtgata       240
gagaacgtat taggcgtgta cggtgggcgc ctataaaagc agagctcgtt tagtgaaccg       300
tcagatcgcc tggagcaatt ccacatacaa acagaccaga ttgtctgttt gttttcgata       360
ttaggatatc gtgtgcatca agtacaaac agaccagatt gtctgtttgt tcagctgcat       420
gcatctcaat tagtcagcaa ctacaaacag accagattgt ctgtttgttg gcagaagtat       480
gatatcactc cgtttaaact acaaacagac cagattgtct gtttgttaca cttttgtctt       540
ataccaactt ccgtaccac ttcctaccct cgtaaattcg aaatcgat                     588

<210> SEQ ID NO 13
<211> LENGTH: 704
<212> TYPE: DNA
<213> ORGANISM: Artificial sequence
<220> FEATURE:
<223> OTHER INFORMATION: MluI-TRE3GCuO6x-ClaI sequence

<400> SEQUENCE: 13
acgcgttact ccctatcagt gatagagaac gtatgaagag tttactccct atcagtgata        60
gagaacgtat gcagacttta ctccctatca gtgatagaga acgtataagg agtttactcc       120
ctatcagtga tagagaacgt atgaccagtt tactccctat cagtgataga gaacgtatct       180
acagtttact ccctatcagt gatagagaac gtatatccag tttactccct atcagtgata       240
gagaacgtat taggcgtgta cggtgggcgc ctataaaagc agagctcgtt tagtgaaccg       300
tcagatcgcc tggagcaatt ccacatacaa acagaccaga ttgtctgttt gttttcgata       360
ttaggatatc gtgtgcatca agtacaaac agaccagatt gtctgtttgt tcagctgcaa       420
catgccttac aaggagagaa atacaaacag accagattgt ctgtttgttc ctaggtttat       480
```

| | |
|---|---|
| atagtgaata gagttaggct acaaacagac cagattgtct gtttgttcag ctgcatgcat | 540 |
| ctcaattagt cagcaactac aaacagacca gattgtctgt tgttggcag aagtatgata | 600 |
| tcactccgtt taaactacaa acagaccaga ttgtctgttt gttacactt tgtcttatac | 660 |
| caactttccg taccacttcc taccctcgta aattcgaaat cgat | 704 |

```
<210> SEQ ID NO 14
<211> LENGTH: 210
<212> TYPE: DNA
<213> ORGANISM: Artificial sequence
<220> FEATURE:
<223> OTHER INFORMATION: CalI-Intron(mP1)-BamHI sequence

<400> SEQUENCE: 14
```

| | |
|---|---|
| gtcaatcgat gctgccgcag caaaagcagg agcagatgcc gccgtcgcag gcgaagatgt | 60 |
| cgcagacgga ggaggcgatg ctgccggcgg aggaggcgaa gtaagtagag ggctgggctg | 120 |
| ggctgtgggg ggtgtggggt gcgggactgg gcagtctggg agtccctctc accactttc | 180 |
| ttacctttct aggatgctgc cggatccgac | 210 |

```
<210> SEQ ID NO 15
<211> LENGTH: 633
<212> TYPE: DNA
<213> ORGANISM: Artificial sequence
<220> FEATURE:
<223> OTHER INFORMATION: ClaI-optiCymR-XhoI sequence

<400> SEQUENCE: 15
```

| | |
|---|---|
| atcgatgcca ccatgtctcc aaagaggaga acccaggcag agagggcaat ggagacacag | 60 |
| ggcaagctga tcgccgccgc cctgggcgtg ctgagggaga agggatacgc aggcttccgc | 120 |
| atcgccgatg tgccaggagc cgccggccgt tcccggggcg cacagtctca ccacttccct | 180 |
| accaagctgg agctgctgct ggccacattt gagtggctgt atgagcagat caccgagagg | 240 |
| agccgcgcca ggctggcaaa gctgaagcca gaggacgatg tgatccagca gatgctggac | 300 |
| gatgccgccg agttctttct ggacgatgac tttagcatct ccctggatct gatcgtggcc | 360 |
| gccgatagag accccgccct gagggagggc atccagagga cagtggagag aaacaggttc | 420 |
| gtggtggagg atatgtggct gggcgtgctg gtgtctcgcg gcctgagccg gatgacgca | 480 |
| gaggacatcc tgtggctgat cttttaacagc gtgcggggcc tggccgtgag atccctgtgg | 540 |
| cagaaggaca aggagcggtt cgagcgcgtg cggaattcca ccctggagat cgccagagag | 600 |
| aggtacgcca agtttaagag atgataactc gag | 633 |

```
<210> SEQ ID NO 16
<211> LENGTH: 1496
<212> TYPE: DNA
<213> ORGANISM: Artificial sequence
<220> FEATURE:
<223> OTHER INFORMATION: SpeI-SV40p- optiHygroR-SV40pA-AgeI sequence

<400> SEQUENCE: 16
```

| | |
|---|---|
| actagtgtgt gtcagttagg gtgtggaaag tccccaggct ccccagcagg cagaagtatg | 60 |
| caaagcatgc atctcaatta gtcagcaacc aggtgtggaa agtccccagg ctccccagca | 120 |
| ggcagaagta tgcaaagcat gcatctcaat tagtcagcaa ccatagtccc gcccctaact | 180 |
| ccgcccatcc cgcccctaac tccgcccagt tccgcccatt ctccgcccca tggctgacta | 240 |
| attttttta tttatgcaga ggccgaggcc gcctctgcct ctgagctatt ccagaagtag | 300 |
| tgaggaggct ttttttggagg ccataggctt ttgcaaaaag ctatgaaaaa gcctgaactc | 360 |

```
acagcgactt ctgttgagaa gtttctgatc gaaaagttcg acagcgttag cgacctgatg      420
cagctctcgg agggcgagga atctagggct ttcagcttcg atgtaggagg gcgtggatat      480
gtcctgcggg taaatagctg cgccgatggt ttctacaaag atcgttatgt ttatcggcac      540
tttgcatcgg ctgcgctccc gattcccgaa gtgcttgaca ttggggagtt cagcgagagc      600
ctgacctatt gcatctcccg ccgcgcacag gcgtaacttt gcaagacctc cctgaaaccc      660
gaactgcccg ctgttctaca acctgtcgcg gaggctatgg acgctattgc tgctgccgat      720
cttccccaga cttccgggtt cggcccattt ggaccgcaag gaatcggtca atacactaca      780
tggcgtgatt tcatttgcgc gattgctgat ccccatgtgt atcattggca aactgtgatg      840
gatgataccg tcagcgcgag tgtcgcgcag gctctcgatg agctgatgct ttgggccgag      900
gattgccccg aagttcgcca cttggtccac gcggatttcg gcagcaacaa tgtcctgaca      960
gataatggcc gcataacagc ggtcattgat tggagcgaag ctatgttcgg ggattcccaa     1020
tacgaggtcg ctaacatctt tttctggcgt ccttggttgg cttgtatgga gcagcaaacg     1080
cgctactttg aaagacgaca tccagagctt gcaggatcgc ctcggctccg gcgtatatg      1140 ctccgcattg tcttgacca actctatcag agcttggtgg acggcaattt cgatgatgct      1200
gcttgggcgc agggtcgatg tgatgcaatc gtccgaagtg gagccgggac tgtcgggcga     1260
acacaaatcg cccgcagaag cgcagccgtc tggaccgatg gctgtgtaga agttctcgcc     1320
gatagtggaa acagacgccc ctctactcgt ccgagggcaa aggaatagaa cttgtttatt     1380
gcagcttata tggttacaa ataaagcaat agcatcacaa atttcacaaa taaagcattt     1440
ttttcactgc attctagttg tggtttgtcc aaactcatca atgtatctta accggt         1496

<210> SEQ ID NO 17
<211> LENGTH: 1979
<212> TYPE: DNA
<213> ORGANISM: Artificial sequence
<220> FEATURE:
<223> OTHER INFORMATION: MluI-CAGGS-BGI (C&R)-MCS-SV40pA-AgeI sequence

<400> SEQUENCE: 17
acgcgtgaca ttgattattg acatgttatt aatagtaatc aattacgggg tcattagttc        60
atagcccata tatggagttc cgcgttacat aacttacggt aaatggcccg cctggctgac       120
cgcccaacga ccccccgccca ttgacgtcaa taatgacgta tgttcccata gtaacgccaa      180
tagggacttt ccattgacgt caatgggtgg agtatttacg gtaaactgcc cacttggcag       240
tacatcaagt gtatcatatg ccaagtacgc cccctattga cgtcaatgac ggtaaatggc       300
ccgcctggca ttatgcccag tacatgacct tatgggactt tcctacttgg cagtacatct       360
acgtattagt catcgctatt accatggtcg aggtgagccc cacgttctgc ttcactctcc       420
ccatctcccc cccctcccca ccccaatttt gtatttatt tattttttaa ttattttgtg       480
cagcgatggg ggcgggggg ggggggggc gcgcgccagg cggggcgggg cggggcgagg       540
ggcggggcgg ggcgaggcgg agaggtgcgg cggcagccaa tcagagcggc gcgctccgaa      600
agtttccttt tatggcgagg cggcggcggc ggcggcccta taaaaagcga agcgcgcggc      660
gggcgttcga aggagtcgct gcgacgctgc cttcgccccg tgccccgctc cgccgccgcc      720
tcgcgccgcc cgccccggct ctgactgacc gcgttactcc cacaggtgag cgggcgggac      780
ggcccttctc ctccgggctg taattagcgc ttggttaat gacggcttgt ttcttttctg       840
tggctgcgtg aaagccttga ggggctccgg gagggccctt tgtgcggggg gagcggctcg      900
```

```
gggggtgcgt gcgtgtgtgt gtgcgtgggg agcgccgcgt gcggctccgc gctgcccggc      960
ggctgtgagc gctgcgggcg cggcgcgggg ctttgtgcgc tccgcagtgt gcgcgagggg     1020
agcgcggccg ggggcggtgc cccgcggtgc gggggggct gcgagggaa caaaggctgc       1080 gtgcggggtg tgtgcgtggg ggggtgagca ggggtgtgg gcgcgtcggt cgggctgcaa      1140
ccccccctgc acccccctcc ccgagttgct gagcacggcc cggcttcggg tgcgggctc      1200 cgtacggggc gtggcgcggg gctcgccgtg ccgggcgggg ggtggcggca ggtgggggtg     1260
ccgggcgggg cggggccgcc tcgggccggg gagggctcgg gggagggggcg cggcggcccc    1320 cggagcgccg gcggctgtcg aggcgcggcg agccgcagcc attgcctttt atggtaatcg     1380
tgcgagaggg cgcagggact tcctttgtcc caaatctgtg cggagccgaa atctgggagg     1440
cgccgccgca cccctctag cgggcgcggg gcgaagcggt gcggcgccgg caggaaggaa      1500
atgggcgggg agggccttcg tgcgtcgccg cgccgccgtc cccttctccc tctccagcct    1560
cggggctgtc cgcgggggga cggctgcctt cgggggggac ggggcagggc ggggttcggc     1620
ttctggcgtg tgaccggcgg ctcttgagcc tctgctaacc atgttcatgc cttcttcttt    1680
ttcctacagc ttcgaacctg gcaacgtgc tggttattgt gctgtctcat cattttggca     1740
aaatcgattg aattctggcc aagtggatcc gctagctcta gagtcgacgg taccagtact     1800
aagcttgcct cgaggatatc ccatggagat ctatggggac atcatgaagc cccttgagca    1860
tctgacttct ggctaataaa ggaaatttat tttcattgca atagtgtgtt ggaatttttt    1920
gtgtctctca ctcggaagga catatgggag catgccctag gcagctgtcc ggaaccggt     1979
```

<210> SEQ ID NO 18
<211> LENGTH: 768
<212> TYPE: DNA
<213> ORGANISM: Artificial sequence
<220> FEATURE:
<223> OTHER INFORMATION: ClaI-optirtTA3G-XhoI sequence

<400> SEQUENCE: 18

```
atcgatgcca ccatgagccg cctggataag tccaaagtga tcaactctgc cctggagctg      60
ctgaatggag tgggaatcga gggactgacc acaaggaagc tggcacagaa gctgggagtg     120
gagcagccta ccctgtactg gcacgtgaag aacaagcgcg ccctgctgga cgcactgcca     180
atcgagatgc tggatcggca ccacacacac agctgcccac tggagggaga gtcctggcag     240
gattttctgc ggaacaatgc caagtcttat agatgtgcac tgctgagcca cagggacgga     300
gcaaaggtgc acctgggaac caggcccaca gagaagcagt acgagaccct ggagaaccag     360
ctggccttcc tgtgccagca gggcttttcc ctggagaatg ccctgtatgc cctgtctgcc     420
gtgggccact ttaccctggg atgcgtgctg gaggagcagg agcaccaggt ggccaaggag     480
gagagagaga caccaaccac agatagcatg ccccctctgc tgaagcaggc catcgagctg     540
ttcgacaggc agggagcaga gccagccttc ctgtttggcc tggagctgat catctgcggc     600
ctggagaagc agctgaagtg tgagtccgga ggacctacag acgcactgga cgatttcgac     660
ctggatatgc tgccagccga tgccctggac gattttgacc tggatatgct gcccgccgac     720
gccctggatg actttgacct ggacatgctg cctggctgat aactcgag                  768
```

<210> SEQ ID NO 19
<211> LENGTH: 765
<212> TYPE: DNA
<213> ORGANISM: Artificial sequence
<220> FEATURE:
<223> OTHER INFORMATION: ClaI-rtTAadv-XhoI sequence

<400> SEQUENCE: 19

```
atcgatgcca ccatgtccag actggacaag agcaaagtca taaacggcgc tctggaatta    60
ctcaatggag tcggtatcga aggcctgacg acaaggaaac tcgctcaaaa gctgggagtt   120
gagcagccta ccctgtactg gcacgtgaag acaagcggg ccctgctcga tgccctgcca   180
atcgagatgc tggacaggca tcatacccac ttctgccccc tggaaggcga gtcatggcaa   240
gactttctgc ggaacaacgc caagtcattc cgctgtgctc tcctctcaca tcgcgacggg   300
gctaaagtgc atctcggcac ccgcccaaca gagaaacagt acgaaaccct ggaaaatcag   360
ctcgcgttcc tgtgtcagca aggcttctcc tggagaacg cactgtacgc tctgtccgcc   420
gtgggccact ttacactggg ctgcgtattg gaggaacagg agcatcaagt agcaaaagag   480
gaaagagaga cacctaccac cgattctatg ccccacttc tgagacaagc aattgagctg   540
ttcgaccggc agggagccga acctgccttc cttttcggcc tggaactaat catatgtggc   600
ctggagaaac agctaaagtg cgaaagcggc gggccggccg acgcccttga cgattttgac   660
ttagacatgc tcccagccga tgcccttgac gactttgacc ttgatatgct gcctgctgac   720
gctcttgacg attttgacct tgacatgctc cccgggtaac tcgag            765
```

<210> SEQ ID NO 20
<211> LENGTH: 1320
<212> TYPE: DNA
<213> ORGANISM: Artificial sequence
<220> FEATURE:
<223> OTHER INFORMATION: XhoI-ires-ECFP-BglII sequence

<400> SEQUENCE: 20

```
ctcgaggccc ctctccctcc ccccccccta acgttactgg ccgaagccgc ttggaataag    60
gccggtgtgc gtttgtctat atgttatttt ccaccatatt gccgtctttt ggcaatgtga   120
gggcccggaa acctggccct gtcttcttga cgagcattcc tagggggtctt tcccctctcg   180
ccaaaggaat gcaaggtctg ttgaatgtcg tgaaggaagc agttcctctg gaagcttctt   240
gaagacaaac aacgtctgta gcgacccttt gcaggcagcg gaaccccca cctggcgaca   300
ggtgcctctg cggccaaaag ccacgtgtat aagatacacc tgcaaaggcg gcacaacccc   360
agtgccacgt tgtgagttgg atagttgtgg aaagagtcaa atggctctcc tcaagcgtat   420
tcaacaaggg gctgaaggat gcccagaagg taccccattg tatgggatct gatctggggc   480
ctcggtgcac atgctttaca tgtgtttagt cgaggttaaa aaacgtcta ggccccccga   540
accacgggga cgtggttttc ctttgaaaaa cacgatgata atatggccac aaccatggtg   600
agcaagggcg aggagctgtt caccggggtg gtgcccatcc tggtcgagct ggacggcgac   660
gtaaacggcc acaagttcag cgtgtccggc gagggcgagg gcgatgccac ctacggcaag   720
ctgaccctga agttcatctg caccaccggc aagctgcccg tgcctggcc cccctcgtg   780
accaccctga cctgggcgt gcagtgcttc agccgctacc ccgaccacat gaagcagcac   840
gacttcttca gtccgccat gcccgaaggc tacgtccagg agcgcaccat cttcttcaag   900
gacgacggca actacaagac ccgcgccgag gtgaagttcg agggcgacac cctggtgaac   960
cgcatcgagc tgaagggcat cgacttcaag gaggacggca acatcctggg gcacaagctg  1020
gagtacaact acatcagcca caacgtctat atcaccgccg acaagcagaa gaacggcatc  1080
aaggccaact tcaagatccg ccacaacatc gaggacggca cgtgcagct cgccgaccac  1140
taccagcaga acacccccat cggcgacggc cccgtgctgc tgcccgacaa ccactacctg  1200
```
agcacccagt ccgccctgag caaagacccc aacgagaagc gcgatcacat ggtcctgctg    1260
gagttcgtga ccgccgccgg gatcactctc ggcatggacg agctgtacaa gtaaagatct    1320

<210> SEQ ID NO 21
<211> LENGTH: 1044
<212> TYPE: DNA
<213> ORGANISM: Artificial sequence
<220> FEATURE:
<223> OTHER INFORMATION: BamHI-optiSB-XhoI sequence

<400> SEQUENCE: 21
ggatccgcca ccatgggcaa gtccaaggag atctctcagg acctgagaaa gaggatcgtg     60
gatctgcaca agagcggcag ctccctggga gcaatctcca gcgcctggc agtgcctcgg    120 tctagcgtgc agaccatcgt gcgcaagtac aagcaccacg gcaccacaca gccttcttat    180
cggagcggcc ggagaagggt gctgagccca cgcgacgagc ggacactggt gcgcaaggtg    240
cagatcaacc cccggaccac agccaaggat ctggtgaaga tgctggagga gaccggcaca    300
aaggtgtcca tctctaccgt gaagagagtg ctgtacagga caacctgaaa gggccactcc    360
gccagaaaga agcctctgct gcagaatagg cacaagaagg caaggctgag gttcgcaacc    420
gcacacggcg acaaggatcg cacattttgg cggaacgtgc tgtggtctga cgagaccaag    480
atcgagctgt tcggccacaa tgatcacaga tacgtgtgga ggaagaaggg cgaggcctgc    540
aagcccaaga ataccatccc tacagtgaag cacggaggag gctccatcat gctgtgggga    600
tgttttgcag caggaggaac aggcgccctg cacaagatcg acggcatcat ggatgccgtg    660
cagtatgtgg acatcctgaa gcagcacctg aagacctctg tgagaaagct gaagctgggc    720
aggaagtggg tgttccagca cgacaacgat ccaaagcaca caagcaaggt ggtggccaag    780
tggctgaagg acaataaggt gaaggtgctg gagtggccca gccagtcccc tgatctgaac    840
ccaatcgaga atctgtgggc cgagctgaag aagagagtga gggcccggag acccaccaac    900
ctgacacagc tgcaccagct gtgccaggag gagtgggcca agatccaccc aaaattactgt    960 ggcaagctgg tggagggcta tcccaagagg ctgacccagg tgaagcagtt taaggcgcaac    1020 gccacaaagt attgataact cgag                                          1044

<210> SEQ ID NO 22
<211> LENGTH: 376
<212> TYPE: DNA
<213> ORGANISM: Artificial sequence
<220> FEATURE:
<223> OTHER INFORMATION: MluI-TREadvCuO32-BGI-ClaI sequence

<400> SEQUENCE: 22
acgcgtgacg aggatcgttc gagcgagttt actccctatc agtgatagag aacgtatgtc     60
gagtttactc cctatcagtg atagagaacg atgtcgagtt tactccctat cagtgataga    120
gaacgtatgt cgagtttact ccctatcagt gatagagaac gtatgtcgag tttactcccc    180
atcagtgata gagaacgtat gtcgagttta tccctatcag tgatagagaa cgtatgtcga    240
gtttactccc tatcagtgat agagaacgta tgtcgaggta ggcgtgtacg gtgggaggcc    300
tatataagca accggtgttt agtgaaccgt cagatctaca aacagaccag attgtctgtt    360
tgttttcgaa atcgat                                                    376

<210> SEQ ID NO 23
<211> LENGTH: 344
<212> TYPE: DNA
<213> ORGANISM: Artificial sequence
<220> FEATURE:
<223> OTHER INFORMATION: TRE3GCuO50 response element sequence

<400> SEQUENCE: 23

| | |
|---|---|
| tccctatcag tgatagagaa cgtatgaaga gtttactccc tatcagtgat agagaacgta | 60 |
| tgcagacttt actccctatc agtgatagag aacgtataag gagtttactc cctatcagtg | 120 |
| atagagaacg tatgaccagt ttactcccta tcagtgatag agaacgtatc tacagtttac | 180 |
| tccctatcag tgatagagaa cgtatatcca gtttactccc tatcagtgat agagaacgta | 240 |
| ttaggcgtgt acggtgggcg cctataaaag cagagctcgt ttagtgaacc gtcagatcgc | 300 |
| ctggagcaat tccacataca aacagaccag attgtctgtt tgtt | 344 |

<210> SEQ ID NO 24
<211> LENGTH: 19
<212> TYPE: DNA
<213> ORGANISM: Artificial sequence
<220> FEATURE:
<223> OTHER INFORMATION: TetO operator sequence

<400> SEQUENCE: 24

| | |
|---|---|
| tccctatcag tgatagaga | 19 |

<210> SEQ ID NO 25
<211> LENGTH: 28
<212> TYPE: DNA
<213> ORGANISM: Artificial sequence
<220> FEATURE:
<223> OTHER INFORMATION: minimal promoter sequence 1

<400> SEQUENCE: 25

| | |
|---|---|
| taggcgtgta cggtgggcgc ctataaaa | 28 |

<210> SEQ ID NO 26
<211> LENGTH: 29
<212> TYPE: DNA
<213> ORGANISM: Artificial sequence
<220> FEATURE:
<223> OTHER INFORMATION: minimal promoter sequence 2

<400> SEQUENCE: 26

| | |
|---|---|
| taggcgtgta cggtgggagg cctatataa | 29 |

<210> SEQ ID NO 27
<211> LENGTH: 28
<212> TYPE: DNA
<213> ORGANISM: Artificial sequence
<220> FEATURE:
<223> OTHER INFORMATION: CuO operator sequence

<400> SEQUENCE: 27

| | |
|---|---|
| tacaaacaga ccagattgtc tgtttgtt | 28 |

<210> SEQ ID NO 28
<211> LENGTH: 324
<212> TYPE: DNA
<213> ORGANISM: Artificial sequence
<220> FEATURE:
<223> OTHER INFORMATION: TRE3GCuO30 response element sequence

<400> SEQUENCE: 28

| | |
|---|---|
| tccctatcag tgatagagaa cgtatgaaga gtttactccc tatcagtgat agagaacgta | 60 |
| tgcagacttt actccctatc agtgatagag aacgtataag gagtttactc cctatcagtg | 120 |

| | |
|---|---|
| atagagaacg tatgaccagt ttactcccta tcagtgatag agaacgtatc tacagtttac | 180 |
| tccctatcag tgatagagaa cgtatatcca gtttactccc tatcagtgat agagaacgta | 240 |
| ttaggcgtgt acggtgggcg cctataaaag cagagctcgt ttagtgaacc gtcagataca | 300 |
| aacagaccag attgtctgtt tgtt | 324 |

<210> SEQ ID NO 29
<211> LENGTH: 332
<212> TYPE: DNA
<213> ORGANISM: Artificial sequence
<220> FEATURE:
<223> OTHER INFORMATION: TREadvCuO32 response element sequence

<400> SEQUENCE: 29

| | |
|---|---|
| tccctatcag tgatagagaa cgtatgtcga gtttactccc tatcagtgat agagaacgat | 60 |
| gtcgagttta ctccctatca gtgatagaga acgtatgtcg agtttactcc ctatcagtga | 120 |
| tagagaacgt atgtcgagtt tactccctat cagtgataga gaacgtatgt cgagtttatc | 180 |
| cctatcagtg atagagaacg tatgtcgagt ttactcccta tcagtgatag agaacgtatg | 240 |
| tcgaggtagg cgtgtacggt gggaggccta tataagcaac cggtgtttag tgaaccgtca | 300 |
| gatctacaaa cagaccagat tgtctgtttg tt | 332 |

<210> SEQ ID NO 30
<211> LENGTH: 352
<212> TYPE: DNA
<213> ORGANISM: Artificial sequence
<220> FEATURE:
<223> OTHER INFORMATION: TREadvCuO52 response element sequence

<400> SEQUENCE: 30

| | |
|---|---|
| tccctatcag tgatagagaa cgtatgtcga gtttactccc tatcagtgat agagaacgat | 60 |
| gtcgagttta ctccctatca gtgatagaga acgtatgtcg agtttactcc ctatcagtga | 120 |
| tagagaacgt atgtcgagtt tactccctat cagtgataga gaacgtatgt cgagtttatc | 180 |
| cctatcagtg atagagaacg tatgtcgagt ttactcccta tcagtgatag agaacgtatg | 240 |
| tcgaggtagg cgtgtacggt gggaggccta tataagcaac cggtgtttag tgaaccgtca | 300 |
| gatcgcctgg agacgccatc ataatacaaa cagaccagat tgtctgtttg tt | 352 |

<210> SEQ ID NO 31
<211> LENGTH: 488
<212> TYPE: DNA
<213> ORGANISM: Artificial sequence
<220> FEATURE:
<223> OTHER INFORMATION: Human beta-globulin intron (BGI) sequence

<400> SEQUENCE: 31

| | |
|---|---|
| tcccggccgg gaacggtgca ttggaacgcg gattccccgt gccaagagtg acgtaagtac | 60 |
| cgcctataga gtctataggc ccacaaaaaa tgctttcttc ttttaatata cttttttgtt | 120 |
| tatcttattt ctaatacttt ccctaatctc tttctttcag gcaataatg atacaatgta | 180 |
| tcatgcctct ttgcaccatt ctaaagaata acagtgataa tttctgggtt aaggcaatag | 240 |
| caatatttct gcatataaat atttctgcat ataaattgta actgatgtaa gaggtttcat | 300 |
| attgctaata gcagctacaa tccagctacc attctgcttt tattttatgg ttgggataag | 360 |
| gctggattat tctgagtcca agctaggccc ttttgctaat catgttcata cctcttatct | 420 |
| tcctcccaca gctcctgggc aacgtgctgg tctgtgtgct ggcccatcac tttggcaaag | 480 |
| aattggga | 488 |

<210> SEQ ID NO 32
<211> LENGTH: 31
<212> TYPE: DNA
<213> ORGANISM: Artificial sequence
<220> FEATURE:
<223> OTHER INFORMATION: Luc-F sequence

<400> SEQUENCE: 32
tcaggatcca tctgcgatct aagtaagctt g                              31

<210> SEQ ID NO 33
<211> LENGTH: 29
<212> TYPE: DNA
<213> ORGANISM: Artificial sequence
<220> FEATURE:
<223> OTHER INFORMATION: Luc-R sequence

<400> SEQUENCE: 33
tcaactcgag ctagaattac acggcgatc                                 29

<210> SEQ ID NO 34
<211> LENGTH: 27
<212> TYPE: DNA
<213> ORGANISM: Artificial sequence
<220> FEATURE:
<223> OTHER INFORMATION: BGI (C&R)-F sequence

<400> SEQUENCE: 34
gtcaatcgat ggagtcgctg cgcgctg                                   27

<210> SEQ ID NO 35
<211> LENGTH: 29
<212> TYPE: DNA
<213> ORGANISM: Artificial sequence
<220> FEATURE:
<223> OTHER INFORMATION: BGI (C&R)-R sequence

<400> SEQUENCE: 35
gtcggatccc tgtaggaaaa agaagaagg                                 29

<210> SEQ ID NO 36
<211> LENGTH: 26
<212> TYPE: DNA
<213> ORGANISM: Artificial sequence
<220> FEATURE:
<223> OTHER INFORMATION: Intron(EF-1a)-F sequence

<400> SEQUENCE: 36
gtcaatcgat gtaagtgccg tgtgtg                                    26

<210> SEQ ID NO 37
<211> LENGTH: 30
<212> TYPE: DNA
<213> ORGANISM: Artificial sequence
<220> FEATURE:
<223> OTHER INFORMATION: Intron(EF-1a)-R sequence

<400> SEQUENCE: 37
gtcggatccc tgaaatggaa gaaaaaaact                                30

<210> SEQ ID NO 38
<211> LENGTH: 30
<212> TYPE: DNA
<213> ORGANISM: Artificial sequence
<220> FEATURE:

```
<223> OTHER INFORMATION: Intron (pSI)-F sequence

<400> SEQUENCE: 38
gtcaatcgat gtaagtatca aggttacaag                              30

<210> SEQ ID NO 39
<211> LENGTH: 25
<212> TYPE: DNA
<213> ORGANISM: Artificial sequence
<220> FEATURE:
<223> OTHER INFORMATION: Intron (pSI)-R sequence

<400> SEQUENCE: 39
gtcggatccc tgtggagaga aaggc                                   25
```